United States Patent
Gupte et al.

(10) Patent No.: US 10,583,295 B2
(45) Date of Patent: Mar. 10, 2020

(54) SYSTEMS AND METHODS TO PROVIDE SYMPATHETIC MODULATION THERAPY

(71) Applicants: Regents of the University of Minnesota, Minneapolis, MN (US); Boston Scientific Scimed, Inc., Maple Grove, MN (US)

(72) Inventors: Akshay Ashok Gupte, Minneapolis, MN (US); Bryan Allen Clark, Forest Lake, MN (US); Bryce Calvin Beverlin, II, St. Paul, MN (US); David Ernest Wechter, San Francisco, CA (US)

(73) Assignees: Regents of the University of Minnesota, Minneapolis, MN (US); Boston Scientific Scimed, Inc., Maple Grove, MN (US)

( * ) Notice: Subject to any disclaimer, the term of this patent is extended or adjusted under 35 U.S.C. 154(b) by 324 days.

(21) Appl. No.: 15/385,103

(22) Filed: Dec. 20, 2016

(65) Prior Publication Data

US 2017/0173340 A1    Jun. 22, 2017

Related U.S. Application Data

(60) Provisional application No. 62/271,094, filed on Dec. 22, 2015.

(51) Int. Cl.
*A61N 1/36* (2006.01)
*A61N 1/05* (2006.01)
*A61N 1/372* (2006.01)

(52) U.S. Cl.
CPC ....... *A61N 1/36139* (2013.01); *A61N 1/0551* (2013.01); *A61N 1/0556* (2013.01);
(Continued)

(58) Field of Classification Search
CPC .............. A61N 1/36139; A61N 1/0556; A61N 1/36071; A61N 1/37205; A61N 1/0551;
(Continued)

(56) References Cited

U.S. PATENT DOCUMENTS

| | | |
|---|---|---|
| 2008/0200972 A1 | 8/2008 | Rittman et al. |
| 2012/0215218 A1* | 8/2012 | Lipani ................ A61B 18/1492 606/41 |

(Continued)

FOREIGN PATENT DOCUMENTS

| | | |
|---|---|---|
| CN | 108778403 A | 11/2018 |
| WO | WO-2006007048 A3 | 12/2008 |
| WO | WO-2017112665 A1 | 6/2017 |

OTHER PUBLICATIONS

"European Application Serial No. 16823474.8, Response filed Mar. 14, 2019 to Communication Pursuant to Rules 161 & 162 dated Sep. 4, 2018", 16 pgs.

(Continued)

*Primary Examiner* — Rex R Holmes
(74) *Attorney, Agent, or Firm* — Schwegman Lundberg & Woessner, P.A.

(57) ABSTRACT

An example of a system may include a lead including a distal electrode portion. The distal electrode portion may be configured to at least partially encircle a sympathetic chain in a lumbar region or thoracic region. The distal electrode portion may include at least one electrode oriented toward the sympathetic chain when the distal electrode portion at least partially encircles the sympathetic chain. The distal portion may include at least one anchoring site configured for use to mechanically secure the distal electrode portion to tissue proximate to the sympathetic chain. The lead may have a strain relief proximate to the distal electrode portion.

20 Claims, 17 Drawing Sheets

(52) U.S. Cl.
CPC ......... *A61N 1/0558* (2013.01); *A61N 1/3605* (2013.01); *A61N 1/36071* (2013.01); *A61N 1/36114* (2013.01); *A61N 1/36117* (2013.01); *A61N 1/36132* (2013.01); *A61N 1/37205* (2013.01); *A61N 1/36057* (2013.01)

(58) Field of Classification Search
CPC .............. A61N 1/36132; A61N 1/0558; A61N 1/3605; A61N 1/36117; A61N 1/36114; A61N 1/36057
See application file for complete search history.

(56) References Cited

U.S. PATENT DOCUMENTS

| | | |
|---|---|---|
| 2013/0165991 A1 | 6/2013 | Kim et al. |
| 2015/0005680 A1 | 1/2015 | Lipani |

OTHER PUBLICATIONS

"International Application Serial No. PCT/US2016/067769, International Preliminary Report on Patentability dated Jul. 5, 2018", 8 pgs.
"International Application Serial No. PCT/US2016/067769, International Search Report dated Mar. 10, 2017", 5 pgs.
"International Application Serial No. PCT/US2016/067769, Written Opinion dated Mar. 10, 2017", 6 pgs.

* cited by examiner

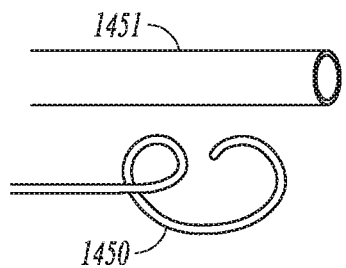
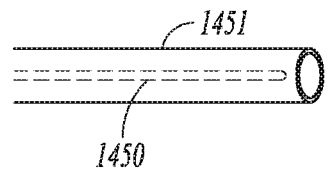
FIG. 14A    FIG. 14B
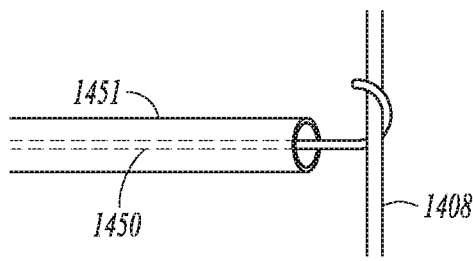
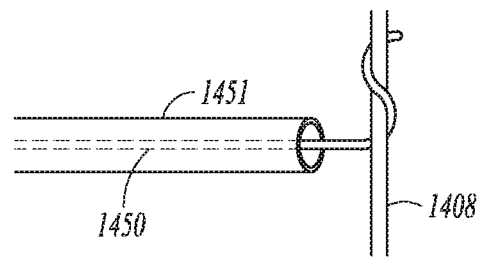
FIG. 14C    FIG. 14D
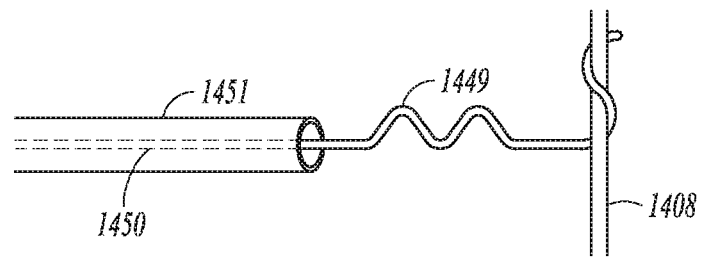
FIG. 14E

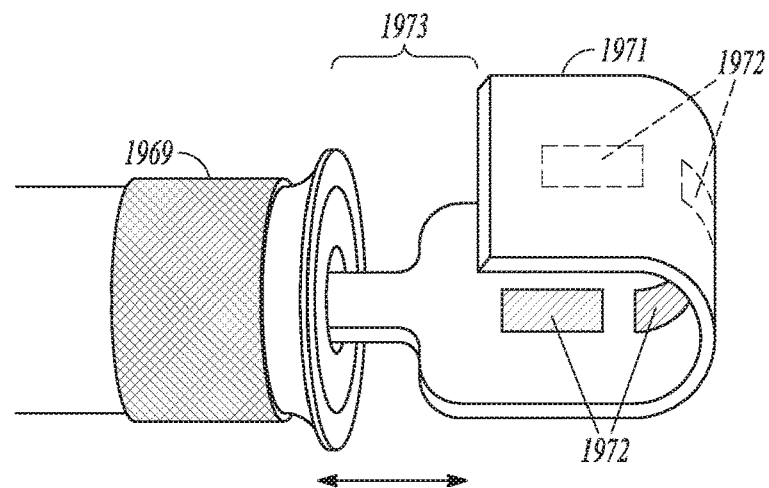
FIG. 19F
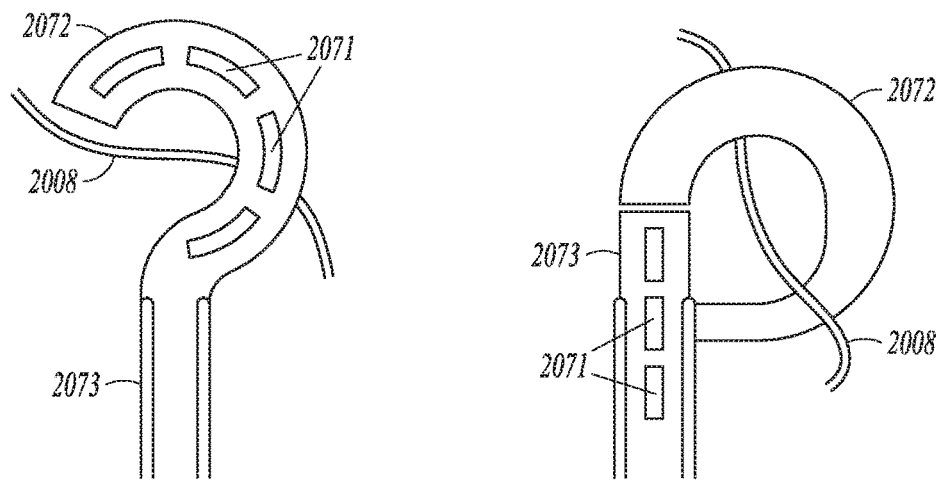
FIG. 20A
FIG. 20B
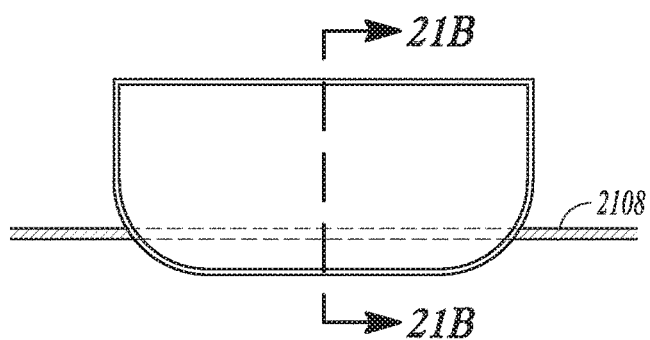
FIG. 21A
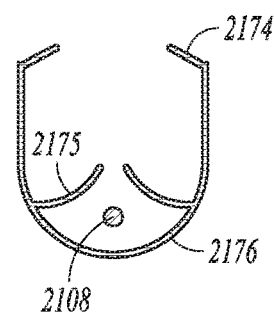
FIG. 21B

SYSTEMS AND METHODS TO PROVIDE SYMPATHETIC MODULATION THERAPY

CLAIM OF PRIORITY

This application claims the benefit of priority under 35 U.S.C. § 119(e) of U.S. Provisional Patent Application Ser. No. 62/271,094, filed on Dec. 22, 2015, which is herein incorporated by reference in its entirety.

TECHNICAL FIELD

This application relates generally to medical systems and methods and, more particularly, to systems and methods to provide sympathetic modulation therapy.

BACKGROUND

Neural modulation has been proposed as a therapy for a number of conditions. Often, neural modulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS, by way of example and not limitation, has been used to treat chronic pain syndromes. Some neural targets may be complex structures with different types of nerve fibers. An example of such a complex structure is the neuronal elements in and around the spinal cord targeted by SCS.

SCS and dorsal root ganglia (DRG) stimulation have been proposed to alleviate pain. A therapeutic goal for conventional SCS programming has been to maximize stimulation (i.e., recruitment) of the dorsal column fibers.

Neuropathic pain patients may not experience adequate pain relief from drugs, or even from spinal cord stimulation (SCS) in many cases. Contributing to the problem is that pain signals communicate via slow-moving unmyelinated type C fibers. Neither SCS nor DRG stimulation achieve maximal coverage of these fibers. Unmyelinated fibers require higher amplitude stimulation to induce action potentials in comparison to myelinated fibers. However, delivery of high amplitude stimulation delivered as part of SCS from the epidural space or delivered proximate to the DRG may be intolerable when other neuronal elements are modulated in the region.

SUMMARY

An example (e.g. "Example 1") of a system may include a lead including a distal electrode portion. The distal electrode portion may be configured to at least partially encircle a sympathetic chain in a lumbar region or thoracic region. The distal electrode portion may include at least one electrode oriented toward the sympathetic chain when the distal electrode portion at least partially encircles the sympathetic chain or is in close proximity to the sympathetic chain. The distal portion may include at least one anchoring site configured for use to mechanically secure the distal electrode portion to tissue proximate to the sympathetic chain. The lead may have a strain relief proximate to the distal electrode portion.

In Example 2, the subject matter of Example 1 may optionally be configured such that the at least one anchoring site is configured for use to be sutured or stapled to a psoas tendon or a psoas muscle, or to a lateral portion of a vertebral body in the lumbar region or the thoracic region.

In Example 3, the subject matter of any one or any combination of Examples 1-2 may optionally be configured such that the lead includes a coiled portion proximate to the distal electrode portion to provide the strain relief or a zig-zag portion proximate to the distal electrode portion to provide the strain relief.

In Example 4, the subject matter of any one or any combination of Examples 1-3 may optionally be configured such that the distal electrode portion includes a distal electrode wrap configured to be wrapped at least 180° around the sympathetic chain in the lumbar region.

In Example 5, the subject matter of any one or any combination of Examples 1-4 may optionally be configured such that the distal electrode portion includes a shape memory that influences the distal electrode portion to a natural wrapped state, the distal electrode portion being configured to encircle the sympathetic chain in the wrapped state.

In Example 6, the subject matter of Example 5 may optionally be configured such that the distal electrode portion includes insulative material, and further includes additional material within the insulative material to provide the shape memory.

In Example 7, the subject matter of Example 5 may optionally be configured such that the distal electrode portion includes a channel to receive a wire to maintain the distal electrode portion in an unwrapped state, wherein removal of the wire allows the distal electrode portion to change into the natural wrapped state.

In Example 8, the subject matter of any one or any combination of Examples 1-8 may optionally be configured such that the distal electrode portion is configured to be wrapped about an axis generally parallel to a distal portion of the lead or is configured to be wrapped about an axis generally perpendicular to a distal portion of the lead.

In Example 9, the subject matter of any one or any combination of Examples 1-4 may optionally be configured such that the distal electrode portion includes an extendible hook configured to extend from a lead body for placement around at least a portion of the sympathetic chain, and to retract toward the lead body to secure the sympathetic chain between the hook and the sheath.

In Example 10, the subject matter of any one or any combination of Examples 1-4 may optionally be configured such that the distal electrode portion includes a hook and a movable clasp configured to move between a retracted position for placement to partially encircle the sympathetic chain and an extended position to secure the sympathetic chain between the hook and the movable clasp.

In Example 11, the subject matter of any one or any combination of Examples 1-10 may optionally be configured to include an implantable modulation device configured to be connected to the lead to deliver neuromodulation energy at a frequency of at least 1 kHz to reversibly block or modulate neural activity in the sympathetic chain.

In Example 12, the subject matter of any one or any combination of Examples 1-10 may optionally be configured to include an implantable modulation device configured to be connected to the lead to deliver neuromodulation energy within a range of 10 Hz to 500 Hz to provide a neurotransmitter depletion block in the sympathetic chain.

In Example 13, the subject matter of any one or any combination of Examples 1-12 may optionally be configured to include an implantable modulation device configured to initiate electrical modulation at a first frequency for a time period less than a minute, and then transition to a second frequency less than the first frequency.

In Example 14, the subject matter of any one or any combination of Example 13 may optionally be configured such that the implantable modulation device is configured to receive a command and to deliver the neuromodulation energy in response to the command for a programmed duration, and automatically stopping delivery of the neuromodulation energy after the programmed duration.

In Example 15, the subject matter of any one or any combination of Examples 13-14 may optionally be configured to include at least one sensor configured to indicate sympathetic nervous system activity or peripheral vascular tone or perfusion, the implantable modulation device including a control circuit operably connected to the at least one sensor and configured to control the neuromodulation energy based on a sensed indication of sympathetic nervous system activity, peripheral vascular tone, perfusion, vascular resistance, temperature or blood glucose.

An example (e.g. "Example 16") of a method may include inserting a trocar or cannulated needle through an entry point and advancing the trocar toward a lateral part of lumber or thoracic spinal vertebra, inserting a lead through the trocar or cannulated needle, the lead including a distal electrode portion having at least one electrode and a strain relief proximate to the distal electrode portion, advancing the distal electrode portion of the lead toward the sympathetic chain in a lumbar region, orientating the distal electrode portion to orient electrodes toward the sympathetic chain under imaging guidance, and anchoring the lead in position to deliver electrical energy through the distal electrode portion to produce a modulation field, and electrically connecting a proximal portion of the lead to an implantable modulation device.

In Example 17, the subject matter of Example 16 may optionally be configured such that the entry point is superolateral to the iliac crest and to midline of spine.

In Example 18, the subject matter of any one or any combination of Examples 16-17 may optionally be configured such that orientating includes orientating the distal electrode portion to orient electrodes away from a psoas muscle.

In Example 19, the subject matter of any one or any combination of Examples 16-18 may optionally be configured such that anchoring includes anchoring the lead to a psoas tendon or a psoas muscle, or to a lateral portion of a vertebral body.

In Example 20, the subject matter of any one or any combination of Examples 16-19 may optionally be configured to include wrapping the distal electrode portion at least 180 degrees around the sympathetic chain.

In Example 21, the subject matter of any one or any combination of Examples 16-20 may optionally be configured such that the distal electrode portion includes a shape memory to wrap around the sympathetic chain and further includes a channel to receive a wire to maintain the distal electrode portion in an unwrapped state, the method further including removing the wire to allow the distal electrode portion to wrap around the sympathetic chain.

In Example 22, the subject matter of any one or any combination of Examples 16-21 may optionally be configured such that the distal electrode portion includes an extendible hook configured to extend from a lead body, the method further comprising extending the hook and placing the extended hook around at least a portion of the sympathetic chain, and retracting the hook toward the lead body.

In Example 23, the subject matter of any one or any combination of Examples 16-22 may optionally be configured such that the distal electrode portion includes a hook and a movable clasp configured to move between and extended position and a retracted position, wherein the method further includes placing the hook to partially encircle the sympathetic chain when the movable clasp is in the retracted position, and extending the movable clasp.

In Example 24, the subject matter of any one or any combination of Examples 16-23 may optionally be configured to include delivering a chemical block, electrical block or cryotherapy block to the sympathetic chain in the lumbar region to test efficacy and determine if a patient is a candidate for sympathetic modulation therapy before inserting the trocar and inserting the lead through the trocar.

In Example 25, the subject matter of any one or any combination of Examples 16-24 may optionally be configured to include using a laparoscopic procedure, where the laparoscopic procedure includes introducing a laparoscope and light into the patient to visualize the distal electrode and the sympathetic chain.

In Example 26, the subject matter of any one or any combination of Examples 16-24 may optionally be configured to include using fluoroscopy, ultrasound or magnetic resonance imaging (MRI) to advance the distal electrode portion of the lead to the sympathetic chain.

An example (e.g. "Example 27") of a method may include electrically modulating neural activity in a sympathetic chain using an implantable modulation device connected to an implanted lead with a distal electrode portion operably positioned proximate to the sympathetic chain in a lumber region or a thoracic region. Electrically modulating may include delivering a neuromodulation energy at a frequency to reversibly block or reduce neural activity in the sympathetic chain. A system may be configured to implement the method. The system may include hardware, software, firmware, or any combination thereof to implement the method. In implementing the method, the system may use a set (or sets) of instructions contained on a computer accessible medium (or media) capable of directing a processor or other controller to perform at least a portion of the method.

In Example 28, the subject matter of Example 27 may optionally be configured such that electrically modulating includes delivering the neuromodulation energy to provide a neurotransmitter depletion block.

In Example 29, the subject matter of any one or any combination of Examples 27-28 may optionally be configured such that electrically modulating includes delivering the neuromodulation energy to provide a conduction depletion block.

In Example 30, the subject matter of any one or any combination of Examples 27-28 may optionally be configured such that electrically modulating includes initiating electrical modulation at a first frequency for a time period less than a minute, and then transitioning to a second frequency less than the first frequency.

In Example 31, the subject matter of any one or any combination of Examples 27-28 may optionally be configured to include receiving a patient command to initiate electrical modulation, and delivering the neuromodulation energy in response to the patient command or an automated system with feedback.

In Example 32, the subject matter of any one or any combination of Examples 27-31 may optionally be configured to include automatically stopping delivery of the neuromodulation energy after a programmed duration.

In Example 33, the subject matter of any one or any combination of Examples 27-32 may optionally be configured such that the programmed duration includes a programmed period of time, a programmed number of delivered pulses, or a programmed amount of delivered charge.

In Example 34, the subject matter of any one or any combination of Examples 27-33 may optionally be configured to include sensing at least one physiological parameter to provide an indication of sympathetic nervous system activity or peripheral vascular tone or perfusion, and automatically controlling the neuromodulation energy based on the indication of sympathetic nervous system activity or peripheral vascular tone or perfusion.

In Example 35, the subject matter of any one or any combination of Examples 27-34 may optionally be configured such that delivering the neuromodulation energy to reversibly block or reduce neural activity in the sympathetic chain is part of a therapy to treat pain, hypertension, heart failure, peripheral vascular disease, ulcers or diabetes.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

FIGS. 14A-E illustrate an example of a self-forming lead configured to be delivered through a catheter.

FIG. 15A is a cross-section view along line 15A-15A in FIG. 15B.

FIGS. 19A-19F illustrate an example of a distal electrode portion that provides a distal hook electrode that is movable with respect to a lead body.

FIGS. 20A-20B illustrate examples of distal electrode portions with segmented electrodes.

FIGS. 21A-21B illustrate an example of a distal electrode portion that has a conformal shape, where FIG. 21B illustrates a cross-section along the line 21B-21B in FIG. 21A.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

By way of example and not limitation, the present subject matter may be used to provide a pain therapy, a therapy to treat complications of peripheral vascular disease such as non-healing ulcers, skin discoloration, paresthesia, a therapy to treat systemic hypertension, or a therapy to treat vasoconstriction. The neuromodulation device may be indicated for patients who suffer from neuropathy such as chemotherapy neuropathy or diabetic neuropathy, peripheral vascular disease, hypertension and heart failure. The pain therapy controls sympathetically-mediated pain. For example, a cancer patient may experience pain because of the cancer itself, the chemotherapeutic treatment, radiotherapy, or a combination thereof. Peripheral vascular disease may be treated using this therapy in lumbar region. Sympathetic inhibition causes vasodilation and thus increased perfusion of tissues of lower extremities. In patients with non-healing or poorly healing ulcers of lower extremities this therapy will promote healing by increasing vascularity of tissues. The neuromodulation device may be indicated for hypertension and/or heart failure patients. Sympathetic modulation or inhibition increases vascular supply to lower extremities by vasodilation of distal vasculature, which increase peripheral pooling of blood in lower extremities and in turn will decrease the cardiac return and load on the heart. This will help reduce cardiac hypertension and also be of assistance in patients with heart failure by this indirect effect.

There are two sympathetic chains. The therapy may include modulation of one (either right or left) or both (both right and left) of these sympathetic chains, dependent upon the patient's symptoms. For example, therapy on the right side to modulate sympathetic activity in the right sympathetic chain may be used to block pain signals from the right leg and also cause vasodilation in the right leg.

Figure 1:
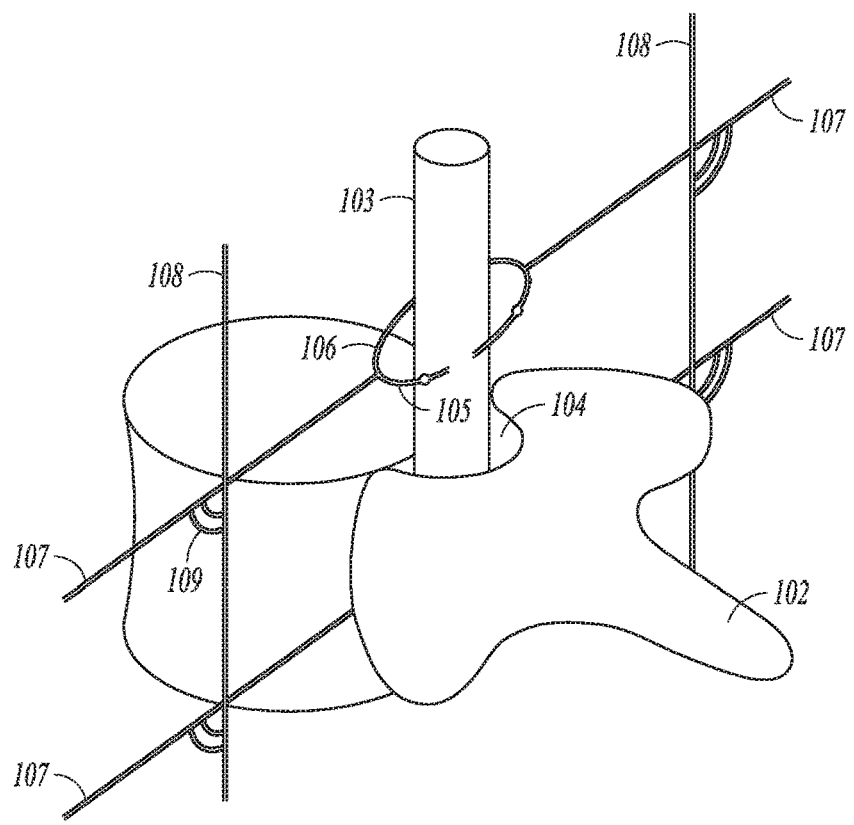
FIG. 1 illustrates a perspective view of a portion of the spinal column.

FIG. 1 illustrates a perspective view of a portion of the spinal column. As illustrated, the vertebrae includes a vertebral body 101 and lamina and spinous process 102 attached to the vertebral body 102. The stacked vertebrae provide a vertebral canal that protects the spinal cord 103. The spinal cord is nerve tissue that carries neural messages between the brain and parts of the body. The spinal cord is surrounded by dura matter, which holds spinal fluid that surrounds the spinal cord. The space between the walls and the dura matter of the vertebral canal is referred to as epidural space 104. Dorsal nerve roots 105 and ventral nerve roots 106 branch off and join, and exit the spine as spinal nerves 107 on both sides through spaces between the vertebrae. FIG. 1 also illustrates a sympathetic chain 108 on each side of the spinal column. The sympathetic chains 108 are a pair of nerve fiber bundles with ganglia in between that run from the base of the skull to the coccyx, and form part of the autonomic nervous system (ANS). The sympathetic chains are connected to each spinal nerve 107 by gray rami and receive fibers from the spinal cord 103 through white rami, and allow neural activity to travel between different levels of spinal nerves 107. The white rami have both myelinated and unmyelinated fibers and provides preganglionic sympathetic outflow from the spinal cord. The gray rami include postganglionic nerve fibers of the sympathetic nervous system. The white and gray rami are illustrated generally at 109

Figure 2:
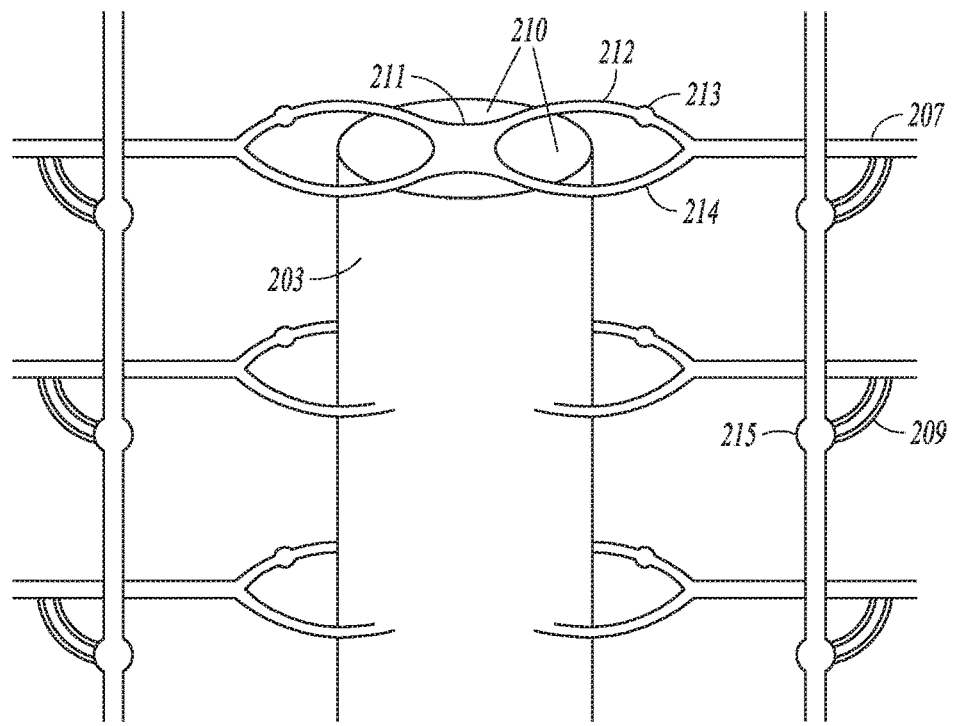
FIG. 2 illustrates a view of the spinal cord without the bony anatomy.

FIG. 2 illustrates a view of the spinal cord 203 without the bony anatomy. The spinal cord 203 includes white matter 210 and gray matter 211. The gray matter 211 includes cell bodies, synapse, dendrites, and axon terminals. Thus, synapses are located in the gray matter. White matter 210 includes myelinated axons that connect gray matter areas. A typical transverse section of the spinal cord includes a central "butterfly" shaped central area of gray matter 211 substantially surrounded by an ellipse-shaped outer area of white matter 210. The white matter of the dorsal column (DC) 210 includes mostly large myelinated axons that form afferent fibers that run in an axial direction. Examples of spinal nerves 207 are also illustrated, including a dorsal root (DR) 212, dorsal root ganglion 213 and ventral root 214. The dorsal root 212 mostly carries sensory signals into the spinal cord, and the ventral root 214 functions as an efferent motor root. The dorsal and ventral roots join to form mixed spinal nerves 207. FIG. 2 also illustrates the sympathetic chains 208 with ganglia 215 and the white and gray rami connecting the sympathetic chains 208 to spinal nerves 207.

Figure 3:
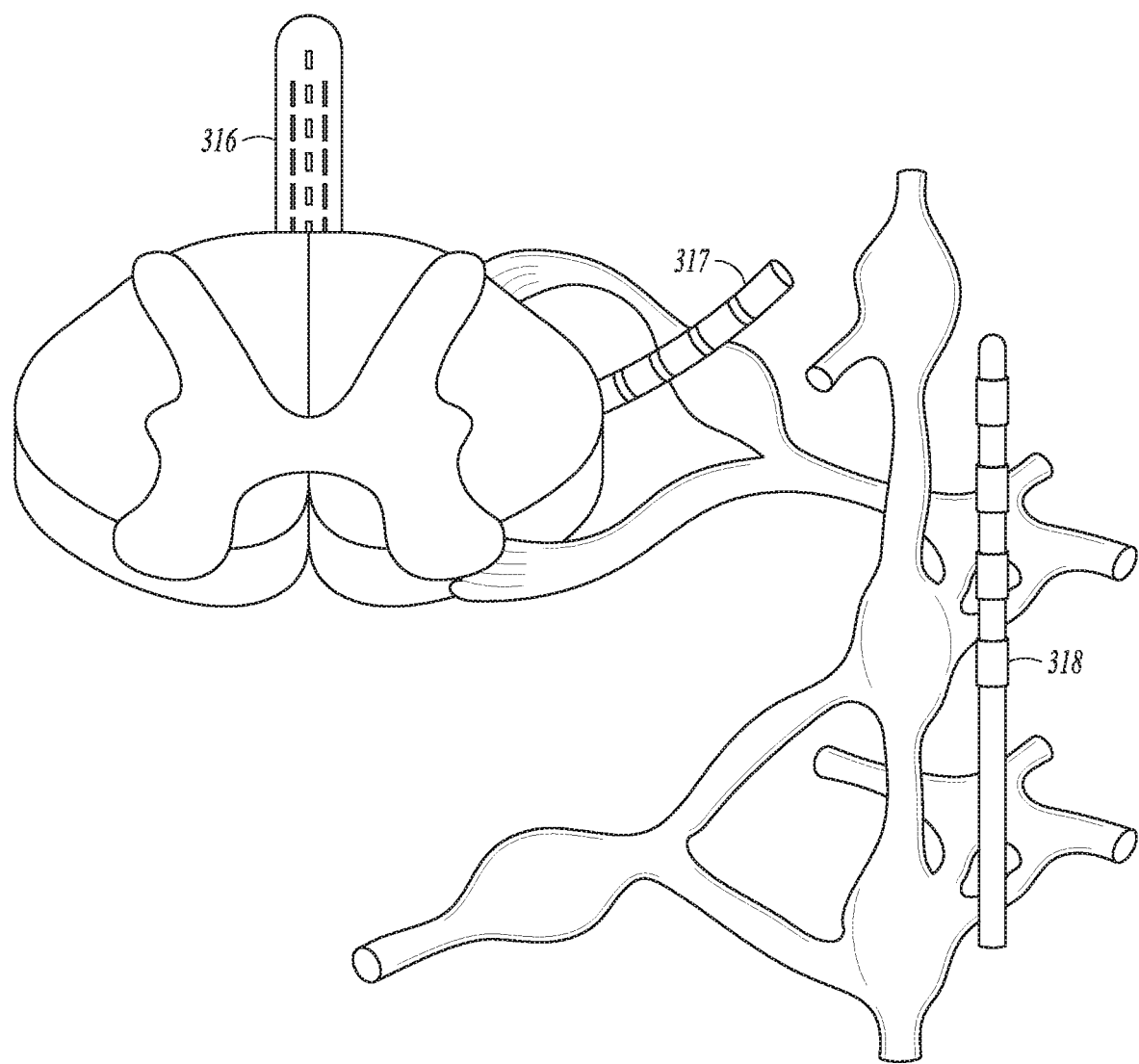
FIG. 3 illustrates a portion of the spinal cord along with illustrations of SCS electrodes in an epidural region to provide SCS, DRG stimulation electrodes to provide DRG stimulation, and sympathetic nerve modulation electrode(s).

FIG. 3 illustrates a portion of the spinal cord along with illustrations of SCS electrodes 316 in an epidural region to provide SCS, DRG stimulation electrodes 317 to provide DRG stimulation, and sympathetic nerve modulation electrode(s) 318. SCS has been used to alleviate pain. A therapeutic goal for conventional SCS programming has been to maximize stimulation (i.e., recruitment) of the dorsal column fibers that run in the white matter along the longitudinal axis of the spinal cord and minimal stimulation of other fibers that run perpendicular to the longitudinal axis of the spinal cord (dorsal root fibers, predominantly). The white matter of the dorsal column includes mostly large myelinated axons that form afferent fibers. While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the dorsal horn of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the dorsal nerve fibers have been targeted for stimulation at an amplitude that provides pain relief. Current implantable neuromodulation systems typically include electrodes implanted adjacent, i.e., resting near, or upon the dura, to the dorsal column of the spinal cord of the patient and along a longitudinal axis of the spinal cord of the patient. Activation of large sensory dorsal nerve fibers also typically creates the paresthesia sensation that often accompanies conventional SCS therapy. Although alternative or artifactual sensations, such as paresthesia, are usually tolerated relative to the sensation of pain, patients sometimes report these sensations to be uncomfortable, and therefore, they can be considered an adverse side-effect to neuromodulation therapy in some cases. Stimulation of the dorsal root ganglia DRG is another technique that has been proposed to provide pain therapy. However DRG stimulation may also cause discomfort.

Neuropathic pain patients may not experience adequate pain relief from drugs, or even from SCS in many cases. Contributing to the problem is that pain signals communicate via slow-moving unmyelinated type C fibers. Neither spinal cord stimulation nor DRG stimulation achieve maximal coverage of these fibers. Unmyelinated fibers such as these C fibers require higher amplitude stimulation to induce action potentials, to inhibit action potentials, or to otherwise modulate neural activity in comparison to myelinated fibers. However, delivery of high amplitude stimulation delivered as part of SCS from the epidural space or delivered proximate to the DRG may be intolerable when other neuronal elements are modulated in the region.

The lumbar region has sympathetic fibers which are away from other spinal nerves. These sympathetic fibers are type C fibers and are unmyelinated, requiring higher amplitude stimulation to induce action potentials, to inhibit action potentials, or to otherwise modulate neural activity. Since these type C, sympathetic fibers in the lumbar region are away from other spinal (myelinated) nerves than the sympathetic fibers at other vertebral levels, higher amplitude may be employed to achieve therapy without side effects caused by undesired modulation of other fibers in the region. It is noted that this relationship of the sympathetic chain in the lumbar region to the neural elements in and near the spinal column also exists for the sympathetic chain in the thoracic reason. The lumbar region is referenced within this disclosure. However, aspects of the present subject matter may be used to modulate or block sympathetic activity in a sympathetic chain within the thoracic region as well.

As will be further described below, various embodiments of the present subject matter target the sympathetic chain in the lumbar region to improve coverage of type C fibers that contribute to pain symptoms. Various embodiments may apply an electrical field to the sympathetic chain to modulate the activity of the sympathetic chain. For example, some embodiments may apply an electrical field to the sympathetic chain to provide a reversible nerve block that produces an effect similar to a sympathectomy, but is reversible. The electrical stimulus may be at a frequency within a range from about 10 Hz to 500 Hz for a neurotransmitter depletion block or at a frequency higher than 1 kHz for a conduction block. It is noted that c-fibers may be depleted at lower frequencies than other fiber types. For example, frequencies within a range of 10 Hz to 50 Hz may be effective to deplete c-fibers, and higher frequencies such as within a range of 50 to 500 Hz may be effective to deplete other types of fibers. A depletion block is discussed in the U.S. patent application Ser. No. 14/597,137, filed Jan. 14, 2015, and entitled "Depletion Block to Block Nerve Communication", which application is incorporated herein by reference in its entirety. The depletion block is less than the frequency to cause a conduction block. The electrical field may be delivered using a train of pulses (e.g. a train of pulses at a steady or changing frequency), or as intermittent neural stimulation using bursts of pulses where the bursts are separated by times without pulses. For example, the frequency of burst may be about 100 Hz, and the frequency of the pulses within a burst may be about 10 kHz.

The sympathetic chain is part of the ANS which is generally discussed below. The ANS regulates "involuntary" organs and maintains normal internal function and works with the somatic nervous system. The ANS includes the sympathetic nervous system and the parasympathetic nervous system. The sympathetic nervous system is affiliated with stress and the "fight or flight response" to emergencies, and the parasympathetic nervous system is affiliated with relaxation and the "rest and digest response."

The ANS regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Afferent nerves convey impulses toward a nerve center, and efferent nerves convey impulses away from a nerve center.

Stimulating or inhibiting the sympathetic or parasympathetic nervous systems can cause heart rate, blood pressure and other physiological responses. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other.

By way of example and not limitation, some embodiments of the present subject matter, for example, modulate neural activity in the sympathetic chain to provide a therapy for pain (e.g. neuropathy) or to provide a therapy for hypertension, heart failure or peripheral vascular disease. According to various embodiments, autonomic neuromodulation may be used to stimulate or inhibit autonomic neural targets in the patient to block or inhibit sympathetic neural activity such as may be useful to treat pain (e.g. neuropathic pain), HF, hypertension and cardiac remodeling, as an increase in sympathetic nerve activity or a reduction in parasympathetic nerve activity contributes to the development and progression of a variety of cardiovascular diseases. Examples of such diseases or conditions include HF, hypertension, and cardiac remodeling. These conditions are briefly described below. In the thoracic region, modulating sympathetic activity has a direct effect on the heart, whereas in the lumbar region, it is more of an indirect effect (through modulation of peripheral vascular tone/vascular resistance, which has an effect on arterial pulsatile pressure and cardiac load). There are a number of disease states that may be treated, such as those that are indicated for sympathectomy or sympathetic blocks including, by way of example and not limitation, CRPS I and II, hyperhidrosis, intractable urogenital pain, amputation stump pain and phantom pain, erythromelalgia, acrocyanosis, and trench foot.

HF refers to a clinical syndrome in which cardiac function causes a below normal cardiac output that can fall below a level adequate to meet the metabolic demand of peripheral tissues. HF may present itself as congestive heart failure (CHF) due to the accompanying venous and pulmonary congestion. HF can be due to a variety of etiologies such as ischemic heart disease. HF patients have reduced autonomic balance, which is associated with LV dysfunction and increased mortality.

Hypertension is a cause of heart disease and other related cardiac co-morbidities. Hypertension occurs when blood vessels constrict. As a result, the heart works harder to maintain flow at a higher blood pressure, which can contribute to HF. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. A large segment of the general population, as well as a large segment of patients implanted with pacemakers or defibrillators, suffer from hypertension. The long term mortality as well as the quality of life can be improved for this population if blood pressure and hypertension can be reduced.

Cardiac remodeling refers to a complex remodeling process of the ventricles that involves structural, biochemical, neurohormonal, and electrophysiologic factors, which can result following a myocardial infarction (MI) or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. The combination of hemodynamic, sympathetic nervous system and hormonal alterations (such as presence or absence of angiotensin converting enzyme (ACE) activity) account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

Various embodiments discussed herein generally relate to providing a therapy to treat peripheral pain and/or vasoconstriction using neuromodulation of spinal chain(s) to block or significantly reduce nerve traffic in the sympathetic chains. A trial process may be implemented to determine if the patient would positively respond with reduced pain symptoms if the sympathetic chain was blocked. For example, a chemical block or electrical block or cryotherapy block may be delivered to temporarily block the neural activity in the sympathetic chain(s). By way of example, the chemical block may be provided using local anesthetics such as lidocaine and ropivacaine. Several locations may be temporarily blocked over several chemical block trials to reduce or completely block sympathetic activity in a portion of the sympathetic chain. If the patient does not have significant pain relief from the chemical block, then it may be determined that the patient is not a likely candidate for the implanted neuromodulator to modulate the sympathetic chain(s). However, if the patient does experience significant pain relief and/or improved peripheral perfusion, then the patient may be considered for an electrical neuromodulator device that can chronically deliver a pain therapy for long-lasting relief, but is still a reversible therapy unlike a sympathectomy which severs the neural pathways.

Figure 4:
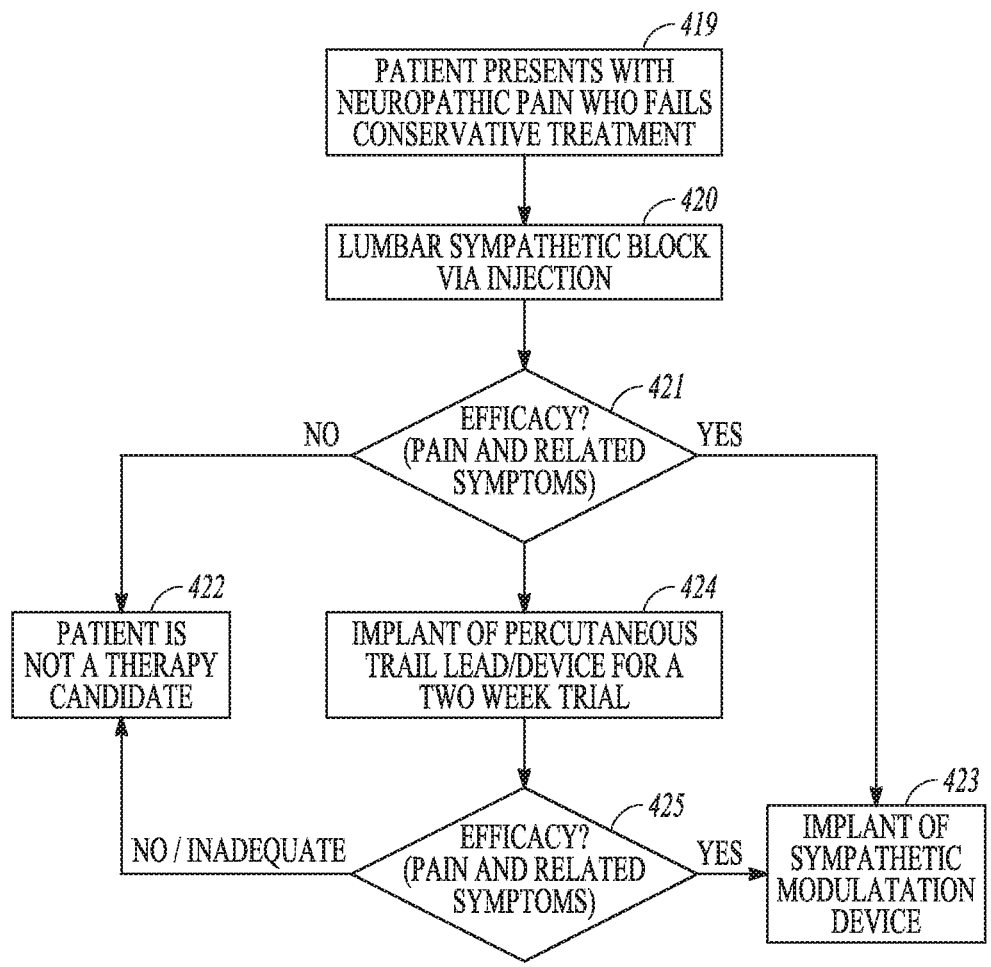
FIG. 4 illustrates, by way of example and not limitation, a process to determine if a patient is a therapy candidate for an implantable modulation device to provide sympathetic modulation therapy to treat neuropathic pain.

FIG. 4 illustrates, by way of example and not limitation, a process to determine if a patient is a therapy candidate for an implantable modulation device to provide sympathetic modulation therapy to treat neuropathic pain. The patient presents with neuropathic pain who fails conservative treatment, as illustrated at 419. At 420, a lumber sympathetic block is injected 420 and efficacy of the injected lumber sympathetic block is determined at 421 such as may be identified by evaluating perfusion, pain and related symptoms. A number of different vertebral levels may be tested with a trial block procedure to determine whether efficacy is or is not likely. The block may be at one or multiple levels, unilaterally or bilaterally. If it is determined that there is no efficacy, it is determined that the patient is not a therapy candidate 422. If it is determined that there is efficacy, it is determined that the patient is a therapy candidate, and the implantable modulation device is implanted to provide the sympathetic modulation 423. If there is some efficacy, a percutaneous trial lead may be implanted, and an external device may be connected to the percutaneous trial lead for a trial period (e.g. on the order of weeks such as two weeks), such as is generally illustrated at 424. The efficacy of the trial is determined at 425. If the trial results in adequate efficacy for pain and related symptoms, the implantable modulation device is implanted to provide the sympathetic modulation 423. Otherwise, if the trial results in inadequate or no efficacy, it is determined that the patient is not a therapy candidate 422.

Figure 5:
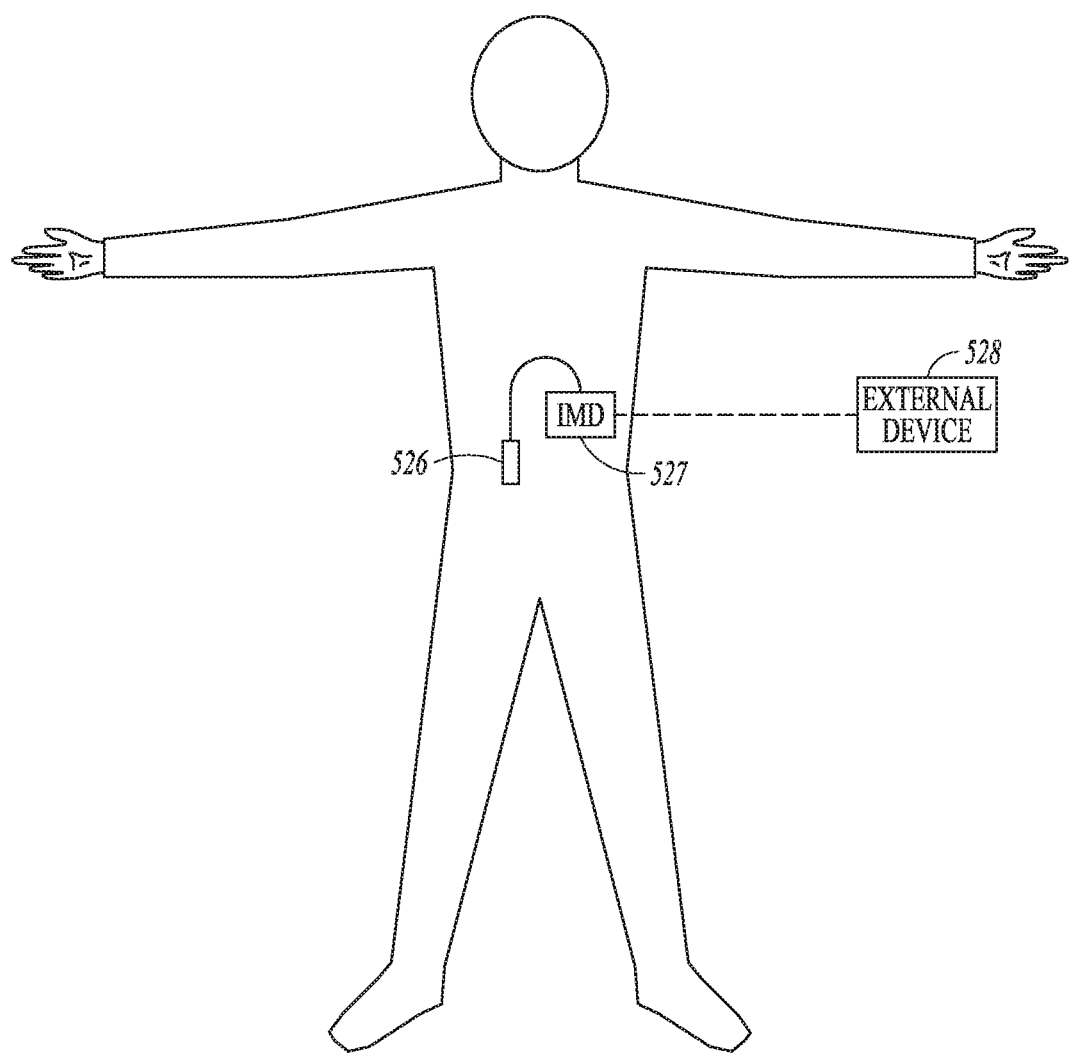
FIG. 5 illustrates an embodiment of an implantable modulation system such as may be used to provide sympathetic modulation therapy in the lumbar region.

FIG. 5 illustrates an embodiment of an implantable modulation system such as may be used to provide sympathetic modulation therapy in the lumbar region. The illustrated system includes electrodes 526, a modulation device 527 and an external system 528. The electrodes 526 are configured to be placed on or near one or more neural targets within a sympathetic chain in a patient or within sympathetic chains for bilateral modulation. The modulation device 527 is configured to be electrically connected to electrodes 526 and deliver neuromodulation energy, such as in the form of electrical pulses, to the one or more neural targets though electrodes 526. The delivery of the neuromodulation is controlled by using a plurality of modulation parameters, such as modulation parameters specifying the electrical pulses and a selection of electrodes through which each of the electrical pulses is delivered. In various embodiments, at least some parameters of the plurality of modulation parameters are programmable by a user, such as a physician or other caregiver. The external system 528 may include a programming device that provides the user with accessibility to the user-programmable parameters.

Figure 6:
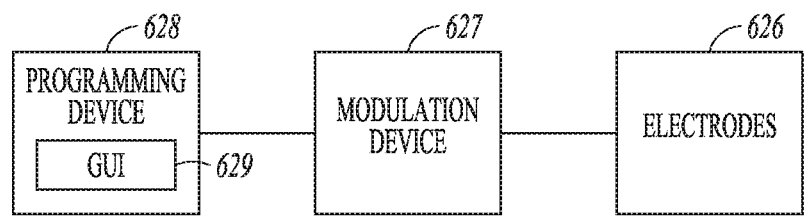
FIG. 6 illustrates, by way of example and not limitation, an implantable modulation system with a programming device, an implantable modulation device, and electrodes.

FIG. 6 illustrates, by way of example and not limitation, an implantable modulation system with a programming device 628, an implantable modulation device 627, and electrodes 626. In various embodiments, the programming device is configured to be communicatively coupled to modulation device via a wired or wireless link. In various embodiments, the programming device 628 includes a graphical user interface (GUI) 629 that allows the user to set and/or adjust values of the user-programmable modulation parameters, and/or that allows the user to provide a command to the modulation device 627 to start an instance of the modulation therapy, such as may occur if the patient is experiencing pain and/or poor circulation in the peripheral extremities. Some embodiments may provide an automated system with feedback. For example, some embodiments may include a sensor, and may be configured to self-adjust the values to account for a change in temperature or perfusion.

The surgical procedure to access the sympathetic chain has an angle of attack as will be described in more detail below. The lead(s) from the neuromodulation electrodes used to modulate the sympathetic chain in the lumbar region extend from the sympathetic chain out toward a subcutaneous space along the angle of attack for the surgical procedure. The lead(s) may be subcutaneously tunneled to the implantable modulation device. The implantable modulation device may be implanted in a surgically-made pocket either in the abdomen or above the buttocks, or may be implanted in other locations of the patient's body. The lead extension(s) may be used to facilitate the implantation of the implantable modulation device in locations further away from the exit point the neuromodulation lead(s).

Figure 7:
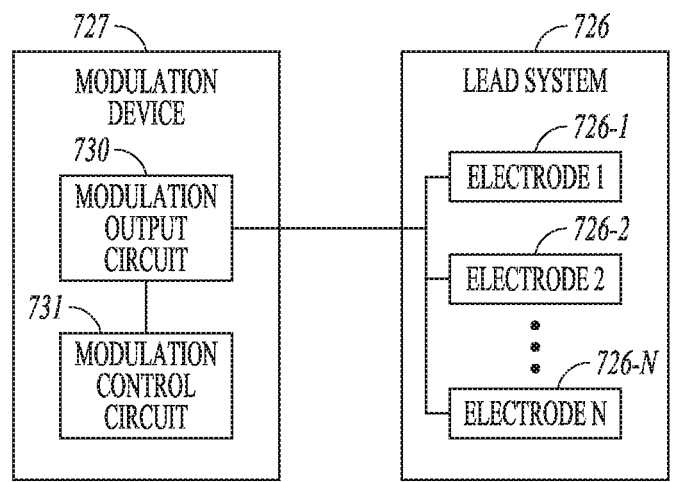
FIG. 7 illustrates an embodiment of a modulation device, such as may be implemented in the neuromodulation system of FIG. 6.

FIG. 7 illustrates an embodiment of a modulation device 727, such as may be implemented in the neuromodulation system of FIG. 6. The illustrated embodiment of the modulation device 727 includes a modulation output circuit 730 and a modulation control circuit 731. Those of ordinary skill in the art will understand that the neuromodulation system may include additional components such as sensing circuitry for patient monitoring and/or feedback control of the therapy, telemetry circuitry and power. The modulation output circuit 730 produces and delivers neuromodulation pulses. The modulation control circuit 731 controls the delivery of the neuromodulation pulses using the plurality of modulation parameters. The lead system 726 includes one or more leads each configured to be electrically connected to modulation device 727 and a plurality of electrodes 726-1 to 726-N distributed in an electrode arrangement using the one or more leads. Each lead may have an electrode array consisting of two or more electrodes, which also may be referred to as contacts. Multiple leads may provide multiple electrode arrays to provide the electrode arrangement. Leads may be used to target multiple vertebral levels to additional areas of the body. Each electrode is a single electrically conductive contact providing for an electrical interface between modulation output circuit 730 and tissue of the patient, where N≥2. The neuromodulation pulses are each delivered from the modulation output circuit 730 through a set of electrodes selected from the electrodes 726-1 to 726-N. The number of leads and the number of electrodes on each lead may depend on, for example, the distribution of target(s) of the neuromodulation and the need for controlling the distribution of electric field at each target. In one embodiment, by way of example and not limitation, the lead system includes two leads each having eight electrodes.

The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, rate (or frequency), ramp speed, duty cycle, pulse shape of the electrical pulses and/or bursts of electrical pulses. Each stimulation burst may include a plurality of neural stimulation pulses and successive neural stimulation bursts may be separated by a time without neural stimulation pulses. A train of neural stimulation bursts may be referred to as intermittent neural stimulation (INS). The time-course of neural stimulation may alternate between intervals of stimulation being ON when pulse(s) are delivered and stimulation being OFF when no pulses are delivered. Each burst includes a plurality of pulses within the burst. The duration of the stimulation ON interval is sometimes referred to as the stimulation duration or burst duration. The time interval between successive NS Events is the INS Interval, which is sometimes referred to as the stimulation period or burst period. For an application of neural stimulation to be intermittent, the stimulation duration (i.e., ON interval) must be less than the stimulation period (i.e., INS Interval) when the neural stimulation is being applied. The duration of the ON interval relative to the INS Interval (e.g., expressed as a ratio) is sometimes referred to as the duty cycle of the INS. Each electrode configuration, along with the electrical pulse parameters, can be referred to as a "modulation parameter set." Each set of modulation parameters, including fractionalized current distribution to the electrodes (as percentage cathodic current, percentage anodic current, or off), may be stored and combined into a modulation program that can then be used to modulate multiple regions within the patient.

Once the leads are correctly positioned, a fitting procedure, which may be referred to as a navigation session, may be performed to program the external control device, and if applicable the neuromodulation device, with a set of modulation parameters that best addresses the painful site and/or site of peripheral vasoconstriction. Thus, the navigation session may be used to pinpoint the volume of activation (VOA) or areas correlating to the pain. The procedure may be implemented to target the tissue during implantation, or after implantation should the leads gradually or unexpectedly move that would otherwise relocate the modulation energy away from the target site. By reprogramming the neuromodulation device (such as by independently varying the modulation energy on the electrodes), the VOA can often be moved back to the effective pain site without having to re-operate on the patient in order to reposition the lead and its electrode array.

Figure 8:
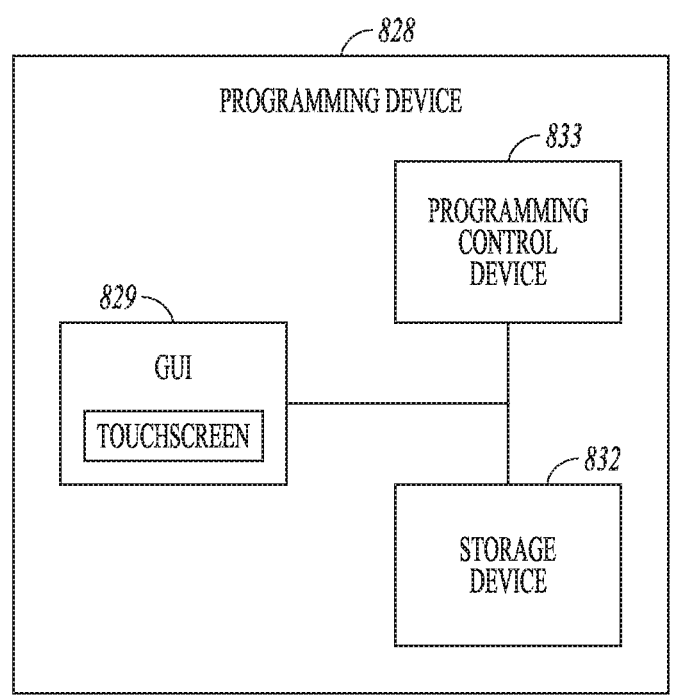
FIG. 8 illustrates an embodiment of a programming device, such as may be implemented as the programming device in the neuromodulation system of FIG. 6.

FIG. 8 illustrates an embodiment of a programming device 828, such as may be implemented as the programming device 628 in the neuromodulation system of FIG. 6. The programming device 828 includes a storage device 832, a programming control circuit 833, and a GUI 829. The programming control circuit 833 generates the plurality of modulation parameters that controls the delivery of the neuromodulation pulses according to the pattern of the neuromodulation pulses. In various embodiments, the GUI 829 includes any type of presentation device, such as interactive or non-interactive screens, and any type of user input devices that allow the user to program the modulation parameters, such as touchscreen, keyboard, keypad, touchpad, trackball, joystick, and mouse. The storage device 832 may store, among other things, modulation parameters to be programmed into the modulation device. The programming device 828 may transmit the plurality of modulation parameters to the modulation device. In some embodiments, the programming device 828 may transmit power to the modulation device. The programming control circuit 833 may generate the plurality of modulation parameters. In various embodiments, the programming control circuit 833 may check values of the plurality of modulation parameters against safety rules to limit these values within constraints of the safety rules.

In various embodiments, circuits of neuromodulation, including its various embodiments discussed in this document, may be implemented using a combination of hardware, software and firmware. For example, the circuit of GUI, modulation control circuit, and programming control circuit, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

As identified above, type C, sympathetic fibers in the lumbar region are further away from other spinal (myelinated) nerves than the sympathetic fibers at other vertebral levels, such that higher amplitude may be employed to achieve therapy without side effects caused by undesired modulation of other fibers in the region. Novel surgical techniques and tools are disclosed herein to implant a neuromodulator to modulate the sympathetic chain(s) in the lumbar region. These techniques may be considered minimally-invasive procedures. Various embodiments introduce electrode(s) for placement operably proximate to the sympathetic chain in the lumbar region to enable electric energy from the electrode(s) to modulate neural activity in the sympathetic chain. For example, an endoscopic/thoracoscopic approach to expose sympathetic chain with instruments within or outside the scope to allow manipulation and potential delivery.

Figure 9:
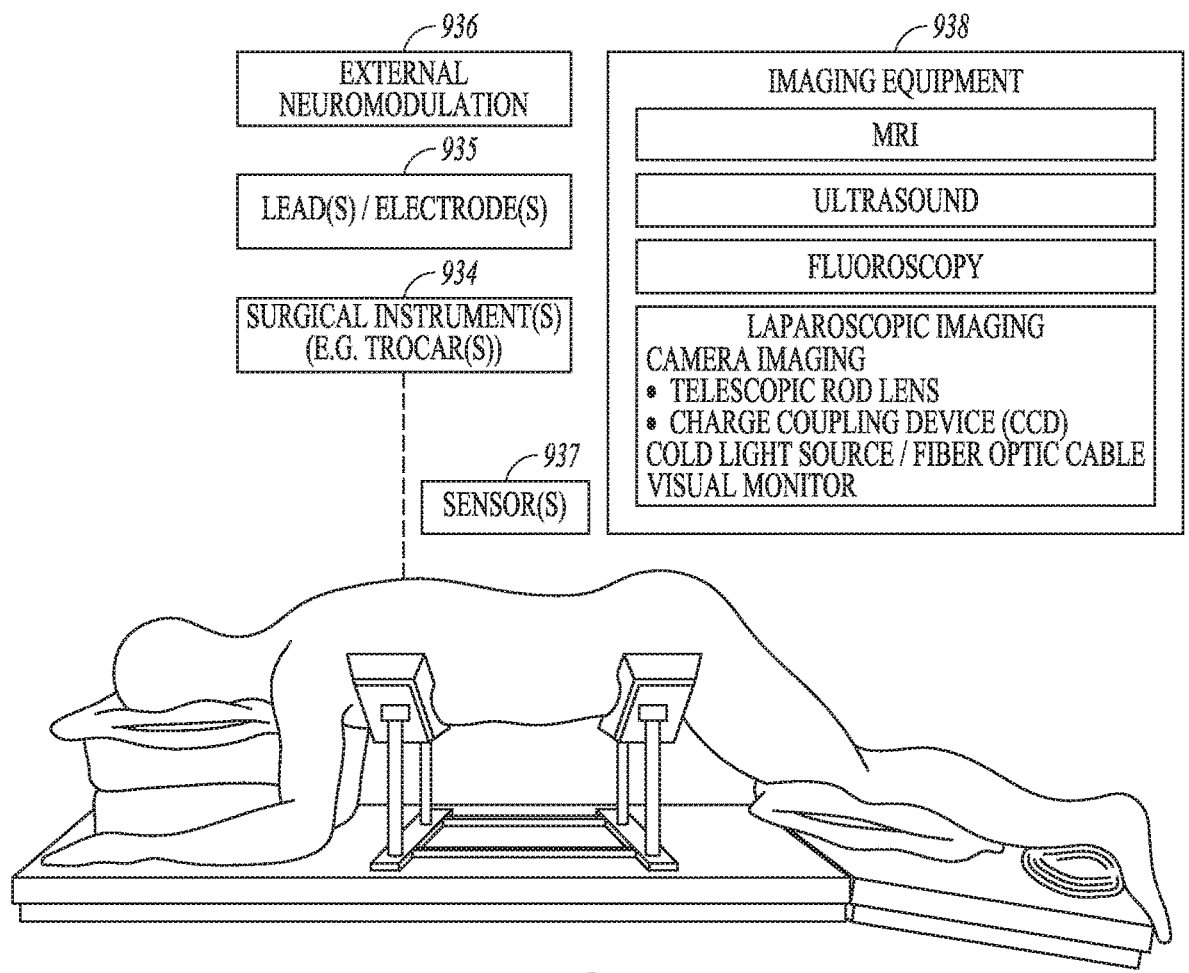
FIG. 9 illustrates a patient and equipment that may be used, according to various embodiments, to perform a surgical procedure to implant a distal electrode portion operably proximate to the sympathetic chain.

FIG. 9 illustrates a patient and equipment that may be used, according to various embodiments, to perform a surgical procedure to implant a distal electrode portion operably proximate to the sympathetic chain. For example, the surgical procedure may include creating an entry point supero-lateral to the iliac crest and to midline of spine. For example, the entry point may be 3 to 4 cm superior to the iliac crest and a few centimeters lateral to midline of spine. The direction from the entry point is towards the lateral part of the lumber spinal vertebra. If the direction is too lateral and deep, vascular complication may occur. The equipment may include surgical instruments such as trocar(s) and other tools that may be inserted through the trocar(s), lead(s) with distal electrode portion(s), an external neuromodulation system and sensor(s) to test efficacy of the placement of the distal electrode portion(s). Imaging equipment, such an ultrasound, fluoroscopy (x-ray) or magnetic resonance imaging (MRI) laparoscopic imaging, may be used to assist with the implantation procedure. Lead delivery may be facilitated with the use of surgical robotic equipment.

By way of example, a laparoscopic approach may be used to provide direct visualization via a scope to enable a surgeon to place electrodes on a sympathetic chain. Laparoscopy is a type of surgical procedure in which a small incision is made through which a laparoscope is inserted which may be used by the doctor to examine the interior of the patient on a video monitor connected to the tube to provide direct visualization of the sympathetic chain. The visualization may be provided by a digital, charge-coupled-device (CCD), commonly referred to as a CCD camera. However, other laparoscopic tools are available such as a rod lens system. Other small incisions can be made to insert instruments to perform procedures. A laparoscopic procedure may inflate the abdomen with carbon dioxide to increase the internal space available for manipulation of surgical instruments. The carbon dioxide may be delivered into the abdomen through the trocar assembly via a gas conduit/port along the side of the trocar assembly or using a needle. Trocar assemblies may include a gas-tight valve to prevent carbon dioxide gas from escaping when instruments are inserted and removed. Also, by way of example, flexible silicone seals can be used to reduce gas leakage when inserting instruments of differing diameter. Other laparoscopic surgical techniques and tools may be used.

The term trocar has been used to refer only to the piercing tip (e.g. stylus), and has also been used to refer to the entire assembly. The present subject matter refers to a trocar assembly, which refers an outer housing assembly, a sleeve that fits inside the housing assembly and a piercing tip protrudes from the lower end of the instrument. The tip may be used to create an opening in the wall of the abdomen. The sleeve may be inserted into the hole and fixed into place. Once inserted through the wall of the abdomen, the tip (stylus) may be removed through the hollow center of the sleeve. A laparoscope or other surgical instruments such as scissors and graspers have been developed to be passed through trocars.

Some embodiments use imaging other than a laparoscope. For example, a trocar assembly may be inserted under fluoroscopy or ultrasound, targeting landmarks, with one or more active electrodes on the trocar. Stimulation may be delivered using different electrodes to determine when the electrodes that are at the targeted location. For example, for each modulation parameter set, a response in the periphery (e.g. temperature, perfusion, vascular resistance, muscle sympathetic nerve activity (MSNA)) may be monitored to determine if the desired location in the sympathetic chain has been modulated. For example, the process may include inserting a lead through a trocar to a targeted location, performing a trial modulation using a first electrode set, determining if the stimulation is successful, changing to a second electrode set and performing the trial modulation using the second electrode set, and repeating until it is determined that the lead includes electrodes(s) that have been successfully positioned, as confirmed via peripheral lower extremity sensors. The implant may be finalized upon finding a successful position. The leads may be attached to the IMD directly or via lead extensions. Multiple electrodes on an electrode device may be placed on the sympathetic chain to provide the system with the ability to try different combinations of electrodes as part of different modulation parameter sets to determine the modulation parameter set that provides the best reduction in pain and/or improvement in perfusion without having to physically move the electrode device.

Laparoscopic access to the sympathetic chain in the lumbar region provides an "angle of attack" but existing leads are too stiff to wrap around the nerve, do not have adequate distal end fixation mechanisms for this neural target, and are not designed with appropriate strain relief proximal to the nerve target to perform adequately in this clinical application. Various embodiments discussed herein provide novel lead designs to provide sympathetic modulation therapy to the sympathetic chain(s) in the lumbar region.

Figure 10:
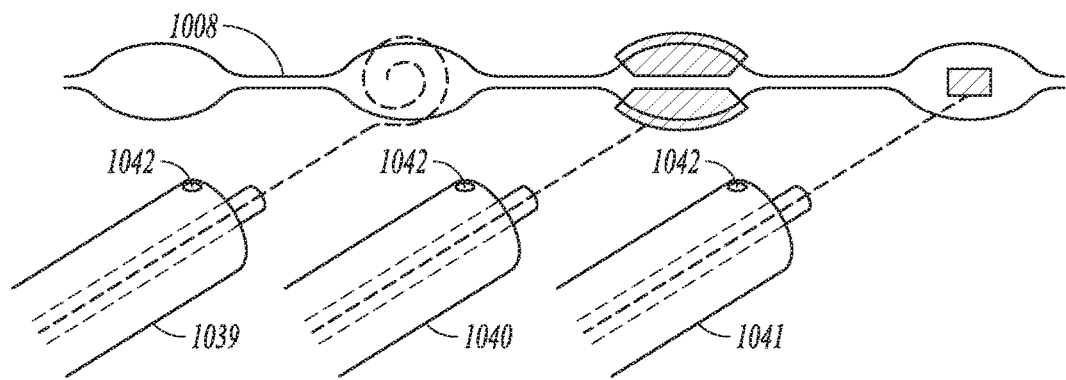
FIG. 10 illustrates, by way of example and not limitation, some embodiments of distal electrode portions.

FIG. 10 illustrates, by way of example and not limitation, some embodiments of distal electrode portions. In one example, the distal electrode portion is configured to wrap around ganglia of the sympathetic chain 1008 through or beside the scope as generally illustrated at 1039. In another example, the distal electrode portion is configured to place a sheet of material containing electrode on or around ganglia as generally illustrated at 1040. In an example, the distal electrode portion is configured to secure an electrode on either side of ganglia as generally illustrated at 1041. A single ganglia or multiple ganglia of the sympathetic chain could be targeted. FIG. 10 also illustrates a camera, such as a CCD camera, that may be incorporated at or near the distal portion of the tool to allow the physician to directly visualize the placement of the distal electrode portions. Separate leads may be placed on the same chain a few mm/cm apart. The distal electrode portion of one lead may function as a cathode and the distal electrode portion of the other may function as an anode. Such positioning may be useful to obtain greater area of nerve capture or capture the plexus rather than just one segment of the nerve. The proximal ends of the lead(s) may be connected to single device.

Figure 11:
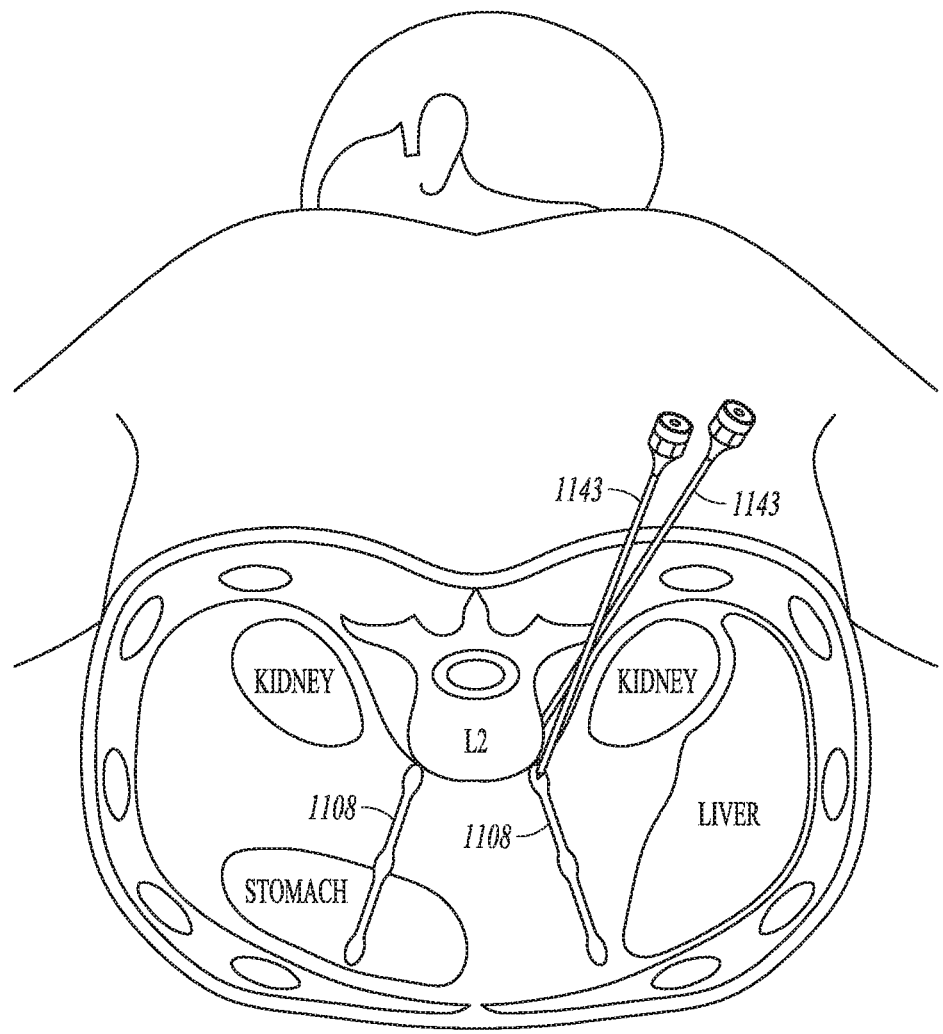
FIG. 11 illustrates, by way of example and not limitation, an embodiment of a percutaneous procedure for implanting the lead(s), where one or more leads are placed through skin, subcutaneous tissue, and muscle near the sympathetic chain.

FIG. 11 illustrates, by way of example and not limitation, an embodiment of a percutaneous procedure for implanting the lead(s), where one or more leads are placed through skin, subcutaneous tissue, and muscle near the sympathetic chain. For example, trocar(s) may be placed close to sympathetic nerves using lumbar vertebra landmarks under fluoroscopy (x-ray), ultrasound or MRI guidance. Two or more trocars may be used, where one may be used to stimulate the neural target and another may be used to record sympathetic nerve activity. Additionally or alternatively, the two or more trocars may be used to stimulate independently or together to assess therapeutic effect at various vertebral levels. If one trocar (or more) are used, perfusion, temperature and sweating changes may be detected of confirm placement of the distal electrode portion. After proper placement of the distal electrode portion is confirmed, the lead may be placed through the trocar and stimulation performed, and the rest of the system with leads and the implantable modulation device may be implanted.

In an example of a process for percutaneously placing leads operationally near a sympathetic chain, a lead is placed through skin, subcutaneous tissue, and muscle near the sympathetic chain. A trocar may be placed under x-ray or ultrasound near the sympathetic chain using landmarks of lumber vertebrae. Lead(s) may be placed through the trocar and trocar maybe removed over it. One or multiple leads may be placed and stimulation trials may be performed. After checking which lead gives good objective placement using a temperature or perfusion sensor, a pressure sensor, or muscle sympathetic nerve activity (MSNA) recording electrode peripherally, for example, the other leads are removed. The best lead(s) is (are) left in and connected to the implantable modulation device.

As provided above, a surgical procedure to access the sympathetic chain follows angle of attack along with the electrode(s) may be inserted and operationally positioned to modulate the sympathetic chain. However, the orientation of the angle of attack and the orientation and position of the sympathetic leads may not align. Therefore, some surgical tools, such as a needle or trocar, used to insert the modulation electrodes may include a mechanism to guide the lead out of the surgical tool to cause the electrode to guide lead out of the needle or trocar in manner to orientate the lead and the modulation electrode(s) on the lead to operationally position the modulation electrode(s) for use to modulate the sympathetic chain. For example, the lead may be guided out of a needle or trocar to lie adjacent to the sympathetic chain or may be guided out of the needle or trocar to partially encircle the sympathetic chain. A distal region of the needle or trocar may include an opening to guide the lead as it exits the needle or trocar in a direction that is not aligned with the angle of attack. By way of example and not limitation, a difference between the orientation of the lead outside of the needle or trocar and the angle of attack and the angle of attack may be between 5 and 90 degrees. In an example, a steerable inner guide catheter may be inserted through the needle or trocar, and a lead may be moved within the catheter. A distal region of the inner guide catheter may be moved to exit the needle or trocar, and steered to direct an end opening of the catheter at an angle that is not aligned with the angle of attack of the surgical procedure. The lead may then be fed out of the end opening of the catheter. Thus, the lead may be guided to lie adjacent to the sympathetic chain or to partially encircle the sympathetic chain.

Some embodiments may use a Seldinger-like approach to place the lead in an operable position to modulate the sympathetic chain. The Seldinger approach may insert a guide wire through a needle, and advance the guidewire toward the targeted region near the sympathetic chain. A dilator may be advanced over the guidewire to create space along the guidewire, and then the dilator may be removed and a catheter can be advanced over the guidewire until an end opening of the catheter is near the targeted region. The guidewire may be removed, and a lead with modulation electrode(s) may be advanced through the catheter to place the modulation electrode(s) in operational position to modulate the sympathetic chain.

Lead designs may configured to provide modulation electrodes to engage with the sympathetic chain in the lumbar region, and to be mechanically secured in position to prevent electrode migration after implantation to maintain efficacy of the modulation and avoid neural injury to the sympathetic chain. Examples of mechanically securing include, but are not limited to, suturing, stapling, screwing, or gluing. Various lead embodiments include strain relief near the distal end of the lead, near the electrodes, to maintain the position of the electrodes. By way of example, one strain relief, which may be relatively small, may be located between the electrode and the distal fixation point to the psoas muscle or tendon, or to a lateral portion of a vertebral body. This strain relief ensures the lead electrodes aren't pulled out of position if the psoas muscle contracts, for example. A second, larger strain relief may be proximal to the fixation point. This larger strain relief may be included to ensure that the entire lead is not translated enough such that it pulls free from the distal fixation point. The sympathetic chain in the lumbar region is near the psoas muscle, which is located along the side of the lumbar region of the vertebral column. Some embodiments of the lead have directional electrode(s) to direct current away from the psoas muscle toward the sympathetic chain.

The shape of the distal end of the lead may have a shape memory to provide the distal end with a self-form function used to wrap at least partially around the nerve. The shape may be held by a number of methods known in the art. For example, the insulative member (polymer) may be molded or otherwise manufactured (e.g. bonded with inner layer in tension relative to outer layer) such that its natural state is in the formed configuration. The insulative member can be made of a biocompatible electrically insulative material known now or later developed for use in implantable leads. By way of example and not limitation, insulative materials may include silicone rubbers, polyurethanes, and co-polymers thereof. In some embodiments, the shape may be held by the conductor(s) and/or additional flexible elastic or superelastic biocompatible materials embedded inside the insulative member. By way of example and not limitation, the materials may include nitinol, Elgiloy, or other suitable biocompatible materials. Rather than use a self-wrapping design, some embodiments use an over-the-wire design where the bias (e.g. helical bias) is in the wire used for delivery.

In some embodiments, the distal end does not possess shape memory to self-form around the nerve. For example, the distal end of the lead may be flexible enough (e.g. with thin silicone insulation and platinum foil electrodes) such that it can be formed/bent around the nerve during lead delivery and then fixated in place.

Some provide a percutaneous lead placed next to the nerve or with a lead that can be wrapped around the nerve to avoid nerve block in other nearby neural fibers or muscle fibers. Various embodiments use a thin, flexible material with electrode(s) to position electrode(s) proximate to the sympathetic chain when the wrap is at least partially wrapped around the sympathetic chain. The material may include silicone, polyurethane, a copolymer thereof, or other suitable biocompatible polymeric material. The wrap includes a least one electrode such as may be used for monopolar stimulation. The wrap may include multiple electrodes for bipolar or multipolar stimulation. The inclusion of a plurality of electrodes provides additional potential electrode vectors to test different modulation fields. The illustrated embodiment includes two electrodes such as may be used for bipolar stimulation. After implantation, the wrap may be sutured, stapled, glued or otherwise mechanically-fixed to itself after it is wrapped around the nerve.

Figure 12A:
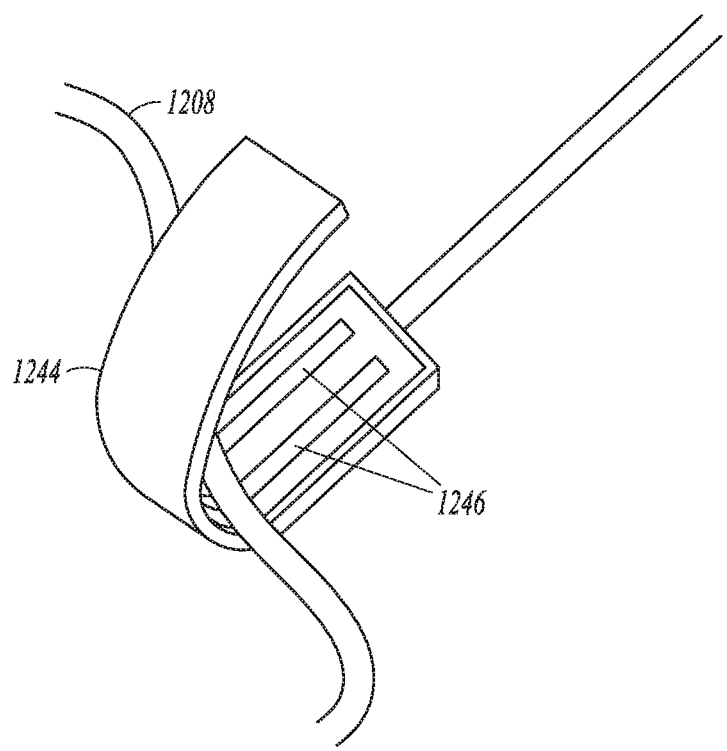
FIGS. 12A and 12B illustrate an example of a distal electrode portion.
Figure 12B:
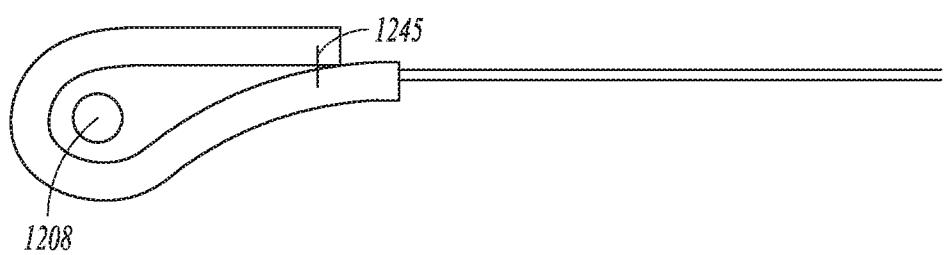

FIGS. 12A and 12B illustrate an example of a distal electrode portion. The illustrated distal electrode portion includes a patch-like substrate that functions as an insulator and at least one electrode on one side of the substrate. One end of the substrate is able to be folded onto the other end to position the electrode(s) in contact with or operationally proximate to the sympathetic chain 1208. For example, the folded sides of the electrode may have a spacing of less than 5 mm. The ends of the patch may be mechanically fixed to each other (e.g. suturing, stapling, gluing, or screwing), such as generally illustrated by the suture 1245 in FIG. 12B. In some embodiments, the electrode(s) may include two or more linear shaped and parallel electrodes 1246 such as may be used to provide an anode and cathode for the electrical modulation. The illustrated embodiment provides a relatively simple procedure to implant electrodes for bipolar modulation. A different number of electrodes may be used, and a different orientation may be used. This design focuses the modulation field toward the sympathetic chain to discourage unintended capture of the psoas muscle or neural elements in and near the spinal column. Also, rather than continuous strips of electrodes, the strips may be replaced by shorter electrodes segments. The electrode segments may reduce distal stiffness, important to wrap around the small neural target.

Various embodiments provide a lead with a distal electrode portion that has shape memory that causes it to function as a self-wrapping lead, and other embodiments do not have the shape memory. The example illustrated in FIGS. 12A-12B may be implemented with or without shape memory. Some embodiments of a distal electrode wrap include super-elastic support material with a natural coiled shape and a center channel into which a wire, such as a stylet or guidewire, may be inserted to uncoil the wrap and may be removed to allow the wrap to coil around the nerve. In some embodiments, the distal electrode wrap is configured to be wrapped at least 180° around the sympathetic chain in the lumbar region.

Figure 13A:
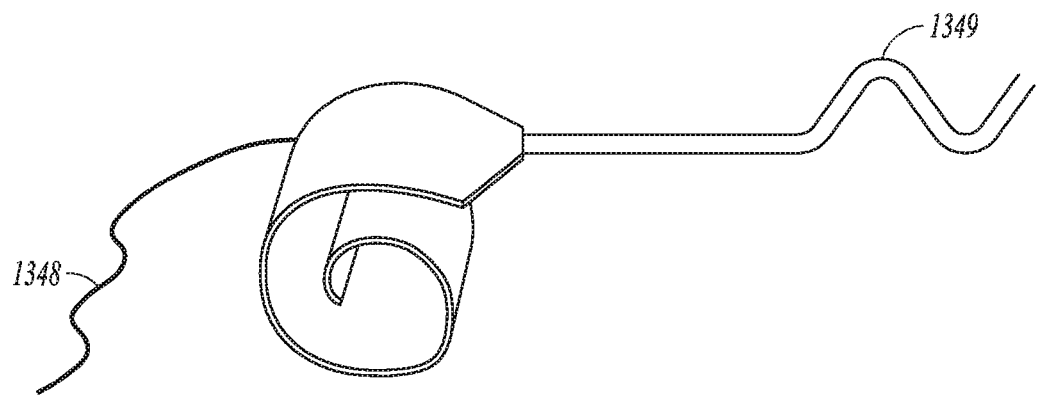
FIGS. 13A-13B illustrate an example of a distal electrode portion with shape memory.
Figure 13B:
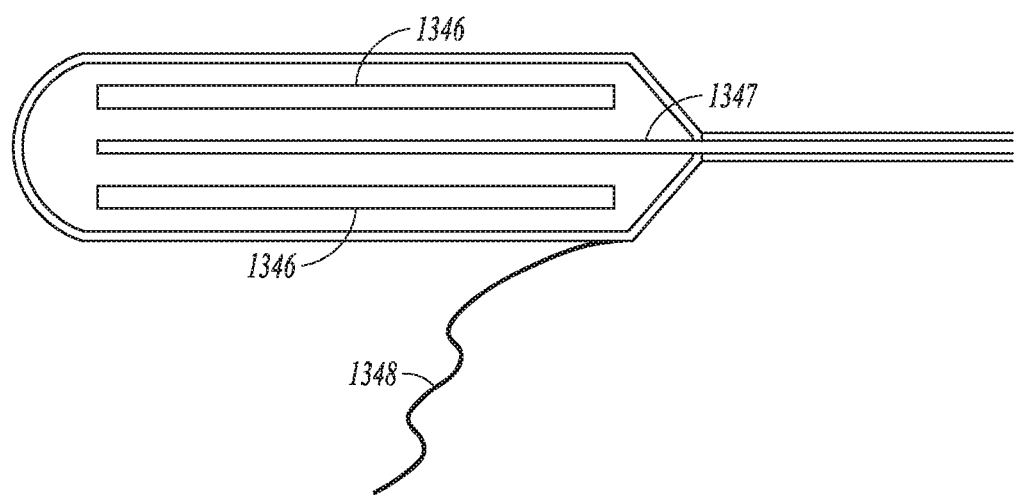

FIGS. 13A-13B illustrate an example of a distal electrode portion with shape memory. For example, FIG. 13A illustrates a view where the wire has been removed from the center channel to allow the distal electrode portion to coil into its natural shape, and FIG. 13B illustrates a view where the wire has been inserted into the center channel 1346. The illustrated embodiment is self-sizing, with an approximately 1-5 mm inner diameter. A suture 1348 may be attached to the lead tip. The suture may be pulled around the distal electrode portion to further fixate the electrode in place around the sympathetic chain and/or may be used to mechanically attach the distal electrode to nearby tissue such as a psoas muscle or psoas tendon. The illustrated lead includes a flexible strain relief region 1349. More than one flexible strain relief regions may be used. Examples of a flexible, strain relief region include a region of coil(s) such as helical-shaped coils, or flexible angle(s) such as zig-zag(s). Preferably, the strain relief is preferably near the distal end (e.g. less than 10 cm) from the electrodes. There may be some variation to accommodate muscle anatomy. A relief will be used between the lead and psoas muscle and a second large strain relief will be between the IPG and the psoas muscle. The spacing between electrodes may be 1 to 10 mm. There may be one electrode such as may be used for monopolar stimulation. The wrap may include multiple electrodes for bipolar or multipolar stimulation, and to provide additional potential electrode vectors to test different modulation fields and/or to span a larger area (e.g. plexus, multiple ganglia) on the sympathetic chain. The illustrated embodiment includes two electrodes.

FIGS. 14A-E illustrate an example of a self-forming lead 1450 configured to be delivered through a catheter 1451, where the lead is fairly straight as it is fed within the catheter (e.g. FIG. 14B), forms in into a shape to wrap around the sympathetic chain 1408 or another neural structure when it is pushed through and exits the catheter FIGS. 14C-14D. The catheter may be removed leaving the lead wrapped around the sympathetic chain, as illustrated in FIG. 14E. The process may include inserting lead into a catheter. When the catheter tip is near the sympathetic chain target, the lead is advanced out of the catheter. As the lead continues to be advanced out of the catheter, its shape memory causes it to be wrapped around the nerve. The lead may have a strain relief 1449 near the distal electrode portion. For example, there may be about 1-10 cm from the proximal end of the electrode contact up to the strain relief. With traction on the lead to keep it in place, the catheter is moved. The lead may be fixated proximal to the electrode and strain relief using a suture, staple, screw, glue or other mechanical fixation means.

Figure 15A:
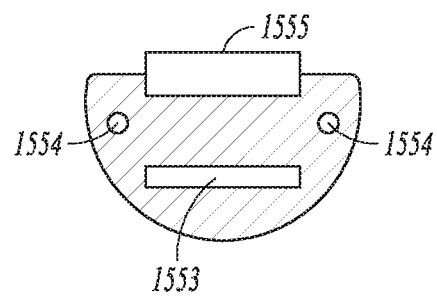
FIGS. 15A-15B illustrate an example of a distal electrode portion, where
Figure 15B:
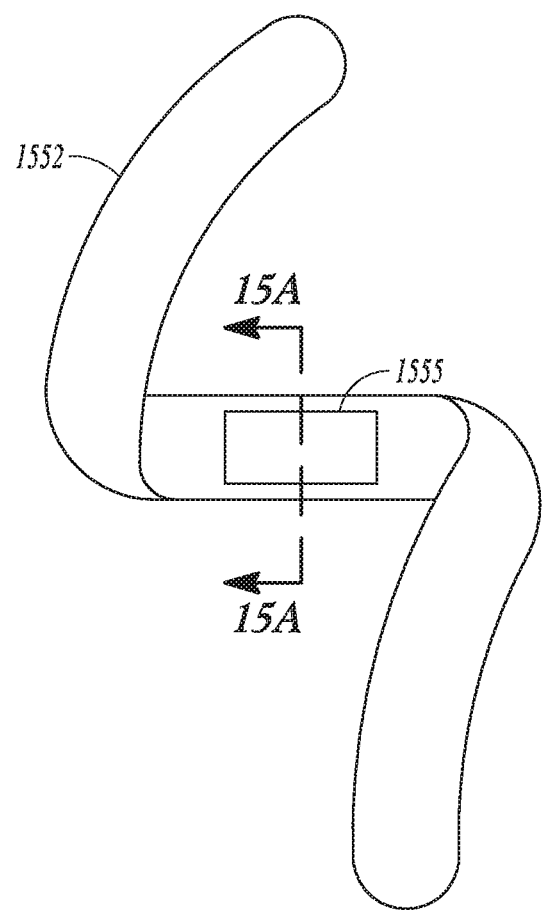

FIGS. 15A-15B illustrate an example of a distal electrode portion, where FIG. 15A is a cross-section view along line 15A-15A in FIG. 15B. The illustrated distal electrode portion has a coil shape and the electrode(s) are on the interior of the coil. The coil may include an insulator 1552 such as silicon, a super-elastic material 1553 such as nitonol, conductor(s) 1554 to distal electrode(s) 1555, and a lubricous coating.

Self-wrapping distal electrical portions may be fabricated using a material to cause the distal electrode portion to tighten further at body temperature. The outer insulation (with electrodes facing towards the nerve) reduce the risks of muscle capture (e.g. capture of the psoas muscle) during stimulation and/or unintended neural capture (e.g. capture of nerves in or near the spinal column).

Some embodiments provide a design that includes at least two distal electrode portions. The two distal electrode portions may be on separate leads, or on a lead (e.g. bifurcated lead) with separate distal lead body portions. Each distal electrode portion may have one electrode, with one of the distal electrode portions having a cathode and another of the distal electrode portions having an anode. In some embodiments, each distal electrode portion may have a cathode and the anode may be located proximally along the lead body or the housing of the implantable modular. In some embodiments, each of the distal electrode portions could have at least two electrodes including at least one anode and at least one cathode spaced about two to ten mm apart for bipolar modulation.

Figure 16A:
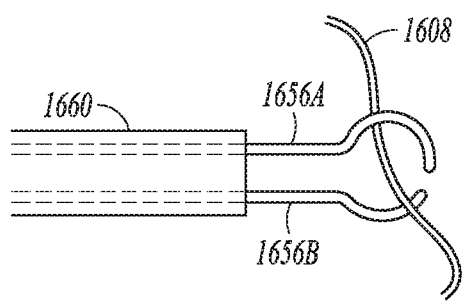
FIG. 16A-16E illustrates an example in which separate lead bodies, each with a distal electrode portion, are connected together about a sympathetic chain.
Figure 16B:
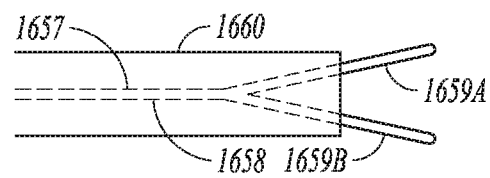
Figure 16C:
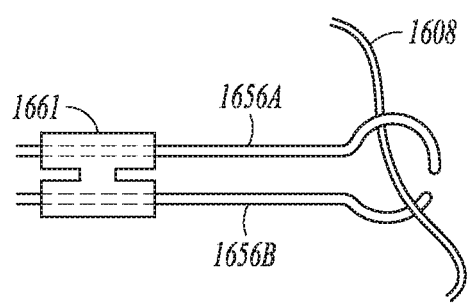
Figure 16D:
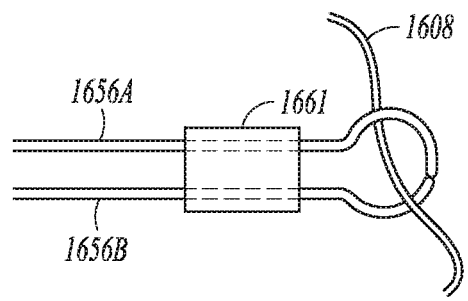
Figure 16E:
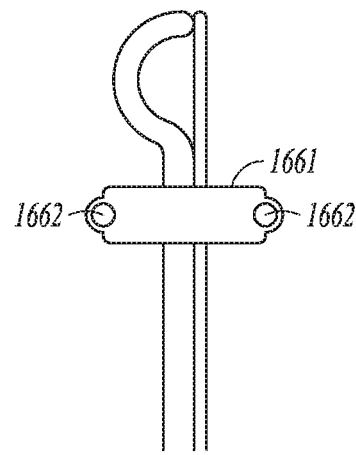

FIG. 16A-16E illustrates an example in which separate lead bodies, each with a distal electrode portion, are connected together about a sympathetic chain 1608. The separate lead bodies 1656A and 1656B may be separate leads, as illustrated in FIG. 16A, each with its own proximal portion that can be connected directly to the implantable modulation device or indirectly via lead extensions. FIG. 16B illustrates a bifurcated lead 1657 that has one proximal portion 1658 and two distal lead bodies 1659A and 1659B each with its own distal electrode portion. The leads may be inserted through a trocar 1660. A snap 1661 or other connector can be moved along the leads toward the distal end such as illustrated in FIGS. 16C-16D, where the snap may be closed using a grasper. As illustrated in FIG. 16E, the snap 1661 to provide the distal electrode portion with an anchoring site 1662 such as an aperture or other configuration to allow the snap to be sutured or stapled or otherwise mechanically secured to nearby tissue such as a psoas muscle or psoas tendon.

Figure 17:
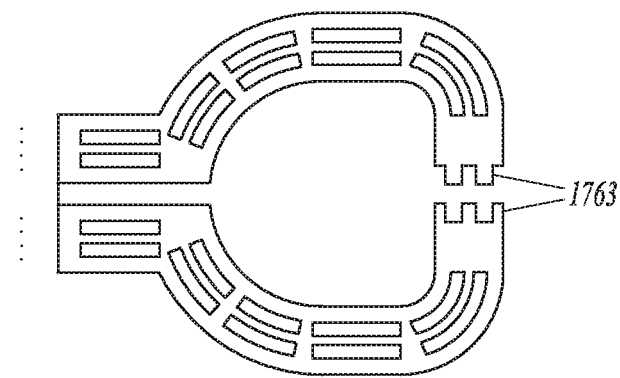
FIG. 17 illustrates an example of a distal electrode portion where the distal ends of the leads are formed with interlocking "teeth" that allow the leads to be pressed together around the spinal chain and maintain the position around the spinal chain.

Some embodiments may use a snapping, or locking, or magnetic closure. FIG. 17 illustrates an example of a distal electrode portion where the distal ends of the leads are formed with interlocking "teeth" that allow the leads to be pressed together around the spinal chain and maintain the position around the spinal chain. In a magnetic embodiment, one of the leads may include a magnet of a first polarity or be formed with magnetism of a first polarity, and the other may include a magnet of a second polarity or be formed with magnetism of the second polarity.

Figure 18A:
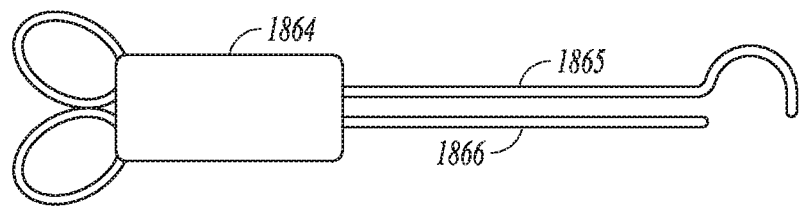
FIGS. 18A-18B illustrate an example of a spring clasp embodiment of a distal electrode portion.
Figure 18B:
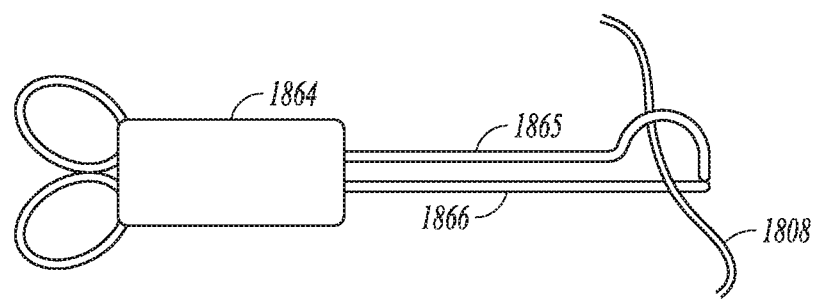

FIGS. 18A-18B illustrate an example of a spring clasp embodiment of a distal electrode portion. Although depicted as a grasper, the proximal end of this figure could be a lead terminal that connects into an IPG. The spring clasp 1864 may include a first lead with a hook 1865 (e.g. J-shaped lead) and a second lead 1866 that may be relatively flat distally and function as a clasp for the hook 1865. The spring clasp 1864 may be designed to allow the flat lead 1866 to be pulled back and latched into a spring-loaded or retracted position as illustrated in FIG. 18A. The flat lead 1866 may be released or translated, using force from the spring, to close an opening into the hook of the first lead as illustrated in FIG. 18B. Thus, a nerve (e.g. sympathetic chain 1808) may be placed in the space that is defined by the hook when the flat lead is latched into the spring-loaded position. The translation of the flat lead encircles the nerve between the hook and the flat lead.

Figure 19A:
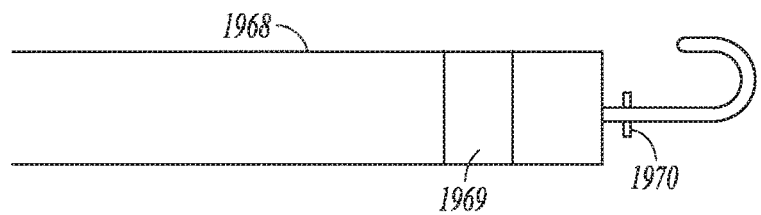
Figure 19B:
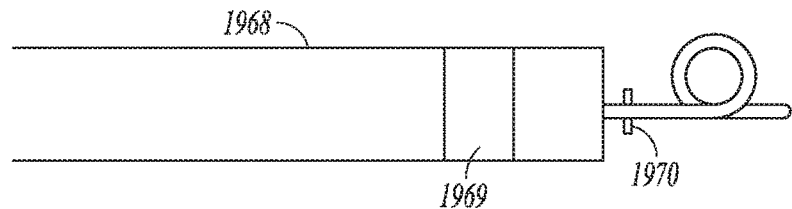
Figure 19C:
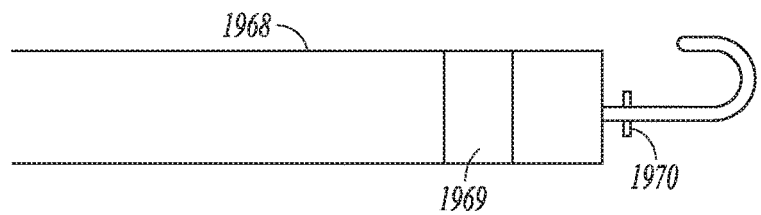
Figure 19D:
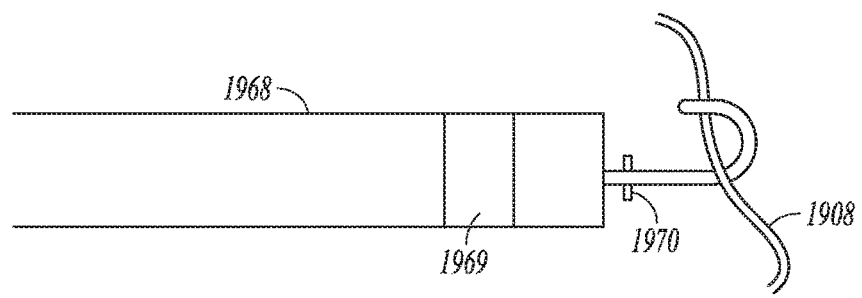
Figure 19E:
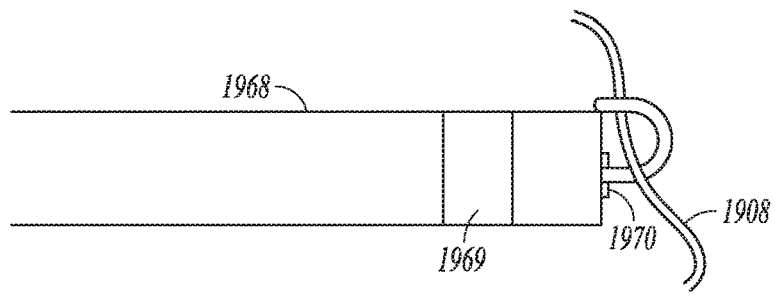
Figure 22A:
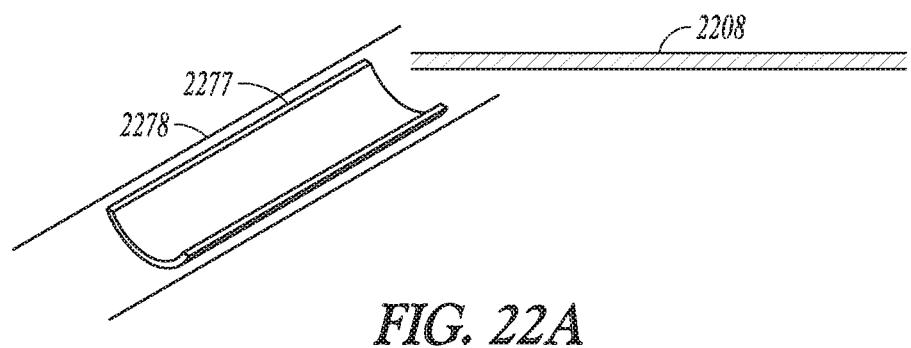
FIGS. 22A-22D illustrate an example of a distal electrode portion that has a partial cylindrical shape that may be delivered within a lumen of a trocar, cannulated needle or other delivery device adjacent to the sympathetic chain or other neural structure.
Figure 22B:
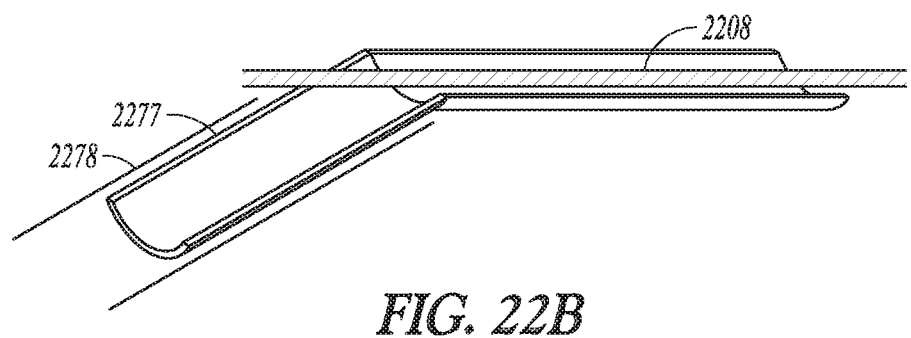
Figure 22C:
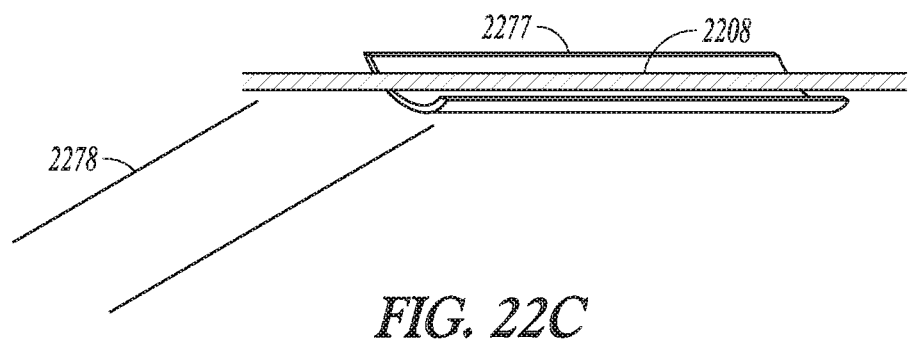
Figure 22D:
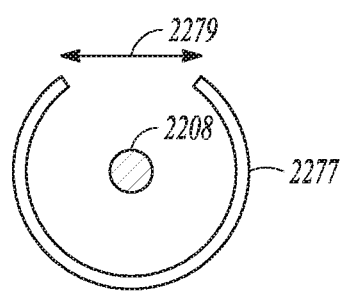

FIGS. 19A-19F illustrate an example of a distal electrode portion that provides a distal hook electrode 1967 that is movable with respect to a lead body 1968. The lead body may include an electrode near its distal portion which may function as an anode, and the hook may include an electrode 1969 which may function as a cathode. In some embodiments, the hook includes at least one electrode that functions as an anode and at least another electrode that functions as a cathode. The clinician may extend the hook electrode from the lead body as illustrated in FIG. 19C, and place the extended hook electrode at least partially around the nerve (e.g. sympathetic chain 1908) as illustrated in FIG. 19D, and then retract the hook electrode 1967 to close an opening defined by the distal hook 1967 and the catheter 1968. Some embodiments may include a mechanical stop 1970 to prevent mechanical injury to neural tissue. The mechanical stop 1970 may be adjustable to accommodate different loop sizes. FIG. 19F illustrates an example of a distal electrode portion that includes a ring electrode 1969, and a hook with an insulative outer material 1971 with electrode(s) 1972 on an inwardly-facing surface of the hook. The insulative outer material may be configured with a rigid or semi-rigid shape memory material embedded to provide the hook with a J-shape. The distal electrode portion is configured to move the hook with respect to the lead body. Some embodiments may have an optional locking or engaging feature 1973.

FIGS. 20A-20B illustrate examples of distal electrode portions with segmented electrodes 2071. The electrical energy delivered to each segmented electrode may be individually controlled. For example, some electrode(s) may be selected to be off, some electrode(s) may be selected to be active and to function as an anode, some electrode(s) may be selected to be active and to function as a cathode, and the fractional contribution of each electrode to the overall modulation field may be individually controlled to provide more selectivity and stimulation paradigms. The process for implanting the electrode may include extending the tip electrode, slipping the hooked end of the tip electrode around the nerve, and locking the tip electrode around the nerve. The segmented electrodes 2071 may be on a hook 2072, may be on a clasp 2072, or may be on both the hook 2072 and the clasp 2073. Furthermore, either the hook 2072 or the clasp 2073 may move with respect to the other to provide an opening to allow the hook to partially encircle the sympathetic chain and to position the distal electrode portion about the sympathetic chain 2008 or other neural structure.

Some electrode embodiments provide a hook with a lead body and a track underneath the lead body. The lead body may include looped edges (e.g. U-shaped edges) configured to partially surround an edge of the track in order to receive the track yet still allow the track to translate with respect to the looped edges of the lead body. The track may function as an electrode. The electrode (track) can move toward the distal loop end to close the loop around the nerve.

FIGS. 21A-21B illustrate an example of a distal electrode portion that has a conformal shape, where FIG. 21B illustrates a cross-section along the line 21B-21B in FIG. 21A. In the illustrated example, the distal electrode portion may have a shape similar to a shape of a hard shell taco with a u-shaped cross-section. The conformal electrode may be made of silicone and polymer to be semi-flexible. The electrical contact(s) may be along the inside, bottom of the u-shape device. Barbs 2174 along the top may be used to tack into a tendon or other tissue. Flaps 2175 may be used to help maintain the nerve 2108 in a channel 2176.

FIGS. 22A-22D illustrate an example of a distal electrode portion 2277 that has a partial cylindrical shape that may be delivered within a lumen of a trocar 2278, cannulated needle or other delivery device adjacent to the sympathetic chain 2208 or other neural structure. The device has the ability to flex as it is positioned near the nerve 2208. The design cups around the nerve like a cuff. The opening may be cinched down (e.g. sutures 2279), around the nerve 2208 to help secure the device around the nerve.

Various embodiments provide the distal electrode portion with an anchoring site to allow the distal electrode portion to be mechanically fixed to tissue. For example, the distal electrode portion may be attached to a psoas tendon or psoas muscle by stapling, suturing, gluing or screwing the anchoring site of the distal electrode portion to the tissue. For example, a silastic patch may have holes for use to secure or staple the patch, and thereby anchor the lead, in the tendon.

Figure 23A:
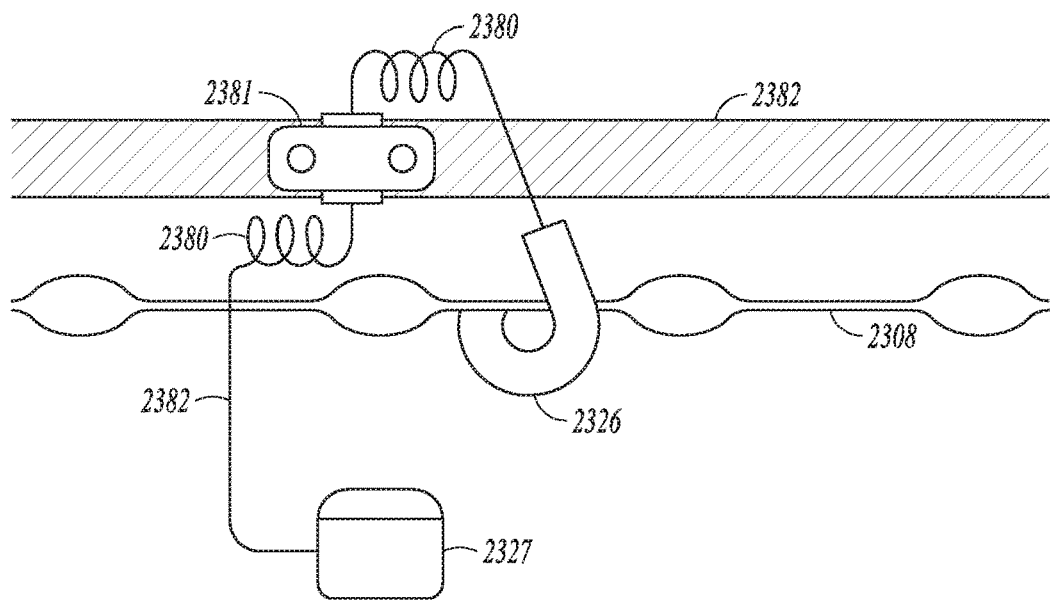
FIGS. 23A-23C illustrate an example of a system that includes an implantable modulation device, a lead including a distal electrode portion for stimulating a sympathetic chain and an anchoring device configured to attach the lead to tissue (e.g. psoas tendon or psoas muscle) near the distal electrode portion.
Figure 23B:
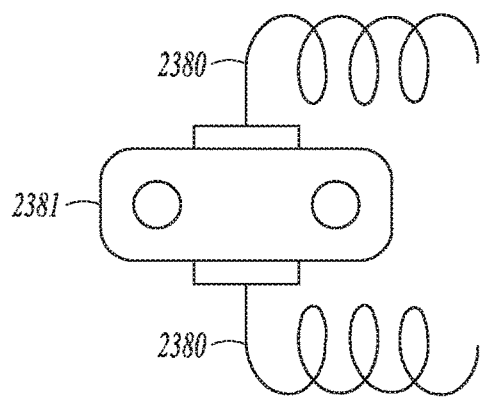
Figure 23C:
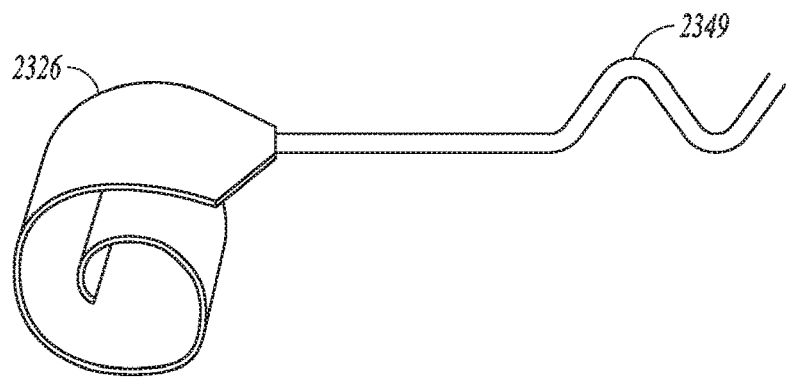

FIGS. 23A-23C illustrate an example of a system that includes an implantable modulation device 2327, a lead 2380 including a distal electrode portion 2326 for stimulating a sympathetic chain 2308 and an anchoring device 2381 configured to attach the lead 2380 to tissue (e.g. psoas tendon 2382 or psoas muscle) near the distal electrode portion 2326. The proximal end of the lead 2380 may be connected to a lead extension 2382 to connect to the implantable modulation device 2327, or the proximal end of the lead 2380 may directly connect to the implantable modulation device 2327. Furthermore, various lead embodiments design a strain relief 2349 as was introduced in the discussion of FIG. 13.

Rather than having a fully-implanted neurostimulator, some embodiments are configured use inductive coupling for transcutaneous energy transfer from an external device to the implantable modulation device and/or to the electrode(s). For example, the lead may be designed to wrap around the nerve. Wire coils in the distal electrode portion or the lead body may be used to pick up inductive current from the external device. A wireless loop may have contacts inside the loop.

The modulation parameter set may include a biphasic and charge-balanced waveform. By way of example, rectangular pulses may be used with a pulse width on the order of 30-100 µs, where pulse width may decrease as pulse frequency increases. The frequency may be a neurotransmitter depletion block (e.g. greater than 10 Hz) or a high frequency (e.g. greater than 1 kHz) that blocks neural activity in the sympathetic chain. The pulse frequency may be at least 5 kHz. In some embodiments, the frequency maybe at least 10 kHz, or at least 20 kHz, or at least 30 kHz (e.g. 50 kHz).

In some embodiments, the waveform may be delivered using current sources to provide a current-controlled waveform on the order of 1-30 mA. The amplitude may increase with increasing frequency. Some embodiments may include multiple independent current controlled sources to each active electrode to provide fractionalized current. For example, individual electrodes can be individually controlled to provide a fraction of the anodic or cathodic current.

In some embodiments, the stimulation is delivered as trains of pulses or intermittently delivered as trains of bursts of pulses. For example, during an ON time, a train of pulses at a pulse frequency may be delivered. No pulses are delivered during an OFF time. The ON/OFF schedule may be a programmed schedule based on time and/or based on pulse counts. In an example, the stimulation may have an on/off cycle with a ratio of 1:3 (i.e. 30 minutes on, 90 minutes off). These times may be lower. However, it may be desired to minimize switching from "on" to "off" because of an onset response with high frequency blocks.

Some embodiments turn on therapy in response to a command based on a sensor input and/or based on a user input. For example, some embodiments provide a patient-activated therapy option to allow the patient to turn on the modulation when the patient is experiencing significant pain. The system may be designed to automatically turn off after a set period of time, or after a set number of pulses, or after a set dose of charge has been delivered to the tissue during a period of time. The automatic turn-off feature may be effective to avoid habituation to the modulation. Some embodiments may allow a patient to modify their own stimulation parameters in order to increase/decrease perception or efficacy. This modification may be made using an external device such as a remote control or other device (e.g. phone) configured to communicate with the implantable modulation device.

A patient may temporarily feel discomfort at relatively lower frequencies, which is referred to as an "onset response." Some embodiment may initiate the therapy at relatively high frequencies (e.g. over 20 kHz) and higher amplitude above a block threshold for which the patient does not experience discomfort. This initial therapy is expected to last a short period of time (on the order of a fraction of a second or seconds such as one or two seconds). The system may then continue to stimulate using a reduce frequency and amplitude, while still staying above the block threshold, for the duration of stimulation session.

The delivered sympathetic modulation block may be intermittent or continuous depending on efficacy. The frequency may be 10 Hz to 50 kHz biphasic waveform. At frequencies exceeding the frequency which nerve fibers can respond, for example greater than 10 Hz for C-fibers and into the hundreds of Hertz range, such as at 100-500 Hz, a neurotransmitter depletion block may be achieved. At relatively higher frequencies, such as 1-50 kHz, a conduction block may be achieved. By way of example, high frequency therapy ranges may be in the 1-10 kHz range.

The current amplitude maybe 1 to 40 mA, and may be delivered for 10 to 30 minutes or more every 6 to 24 hours. An intermittent high-frequency block may be followed by continuous or intermittent lower frequency blockade, such as 100 to 2000 Hz at <10 mA. The stimulation pattern may be dynamic, changing over time, so the body is less able to adapt and compensate over time. The pattern may be random or pseudorandom.

Some embodiments provide a closed-loop therapy to control the implantable modulation device. An algorithm of two or more physiological parameters may be used to provide the closed-loop control to provide a more reliable therapy as any one physiological parameter may not correlate perfectly with when therapy is needed, particularly taking into a wide range of patient activities. For example, an electrical sensor may be located cranial to electrodes to assess afferent blockade or caudal to electrode to assess efferent blockade. A chemical sensor may be used to monitor neurotransmitters. Other sensors include a peripheral blood pressure sensor, a peripheral perfusion sensor, a peripheral temperature sensor, heart rate sensor, heart rate variability, galvanic skin resistance (GSR) sensor, and a position sensor.

For example, sensors may be used to monitor HRV to provide a measure of sympathetic tone. The modulation may be activated therapy when SDNN (a standard deviation of intervals between ventricular contractions (RR intervals)) or other measure of HRV such as RMSSD and SDNN/RMSSD, is below threshold. The GSR may provide a measure of sympathetic tone by detecting increased secretion of sweat glands. Therapy may be activated when GSR above threshold. Skin temperature (peripheral, lower limb) may provide a measure that provides an indication of vasoconstriction, as vasoconstriction causes reduced skin temperature. Therapy may be activated when skin temperature is below threshold. Similarly, a flow sensor or perfusion sensor may sense peripheral blood flow in the lower limb. A Photoplethysmograph (PPG) may detect low flow or low perfusion, which provides an indication of vasoconstriction. Therapy may be activated when a measure of perfusion or flow is below a threshold. A blood pressure sensor may be used to detect sympathetic tone, as increased sympathetic tone causes vasoconstriction and thus elevated blood pressure in the periphery. The therapy may be activated to reduce blood pressure in response to a detected, elevated blood pressure. A neural sensor may be used to detect and record action potentials in the sympathetic chain. Therapy may be activated when nerve activity exceeds threshold. Additionally or alternatively, the neural sensor may be used at initial patient set-up to determine patient-specific block thresholds for stimulation parameter(s) such as amplitude, frequency, and the like. For example, a brief amount of stimulus (e.g. 5 kHz, 7 mA) may be delivered and the action potentials may be monitored post-stimulus, and repeated using different modulation parameter sets until adequate suppression is observed. A posture sensor (e.g. 3-axis accelerometer), may be used to determine if patient is lying down or standing, which can be used as an input to therapy to modulate blood pressure swings when changing positions. Thus, for example, blood pressure may be allowed to increase to avoid syncope if the patient is moving into a standing position. The sensor(s) may be implanted or worn (e.g. patch). Some closed loop systems modulate the therapy based on exacerbation of symptoms as may be detected using sensor(s).

The neuromodulation device may be indicated for patients who suffer from neuropathy such as chemotherapy neuropathy or diabetic neuropathy, peripheral vascular disease, hypertension and heart failure. The neuromodulation device may be indicated for diabetes as it may assist in indirect insulin regulation. The device may be implanted to modulate sympathetic activity in the thoracic region rather than the lumbar region. The therapy may be activated to modulate glucose release/insulin production. A glucose sensor may be used to implement the therapy.

An acute animal test (n=4) was conducted in which hind limb blood flow was measured while delivering neurostimulation to the sympathetic chain. Stimulation was delivered at 5 kHz, and stimulation was increased in steps up to 10 mA of current. For about the first 10 seconds of stimulation at a low level of current, it was observed that the blood flow initially decreased and the heart rate initially increased. After about 10 seconds, it was observed that there was a sustained response that increased blood flow even for some time (minutes) after the stimulation was turned off.

Additionally, a chronic animal test (n=3 animals) was conducted where the impact of stimulation on unintended muscle capture, heart rate and blood pressure were assessed. It was observed that lower frequency stimulation (e.g. between 10 to 120 Hz) was tolerated less than higher frequency stimulation (e.g. between 300 to 10,000 Hz). For example, slight muscle tension was observed at 120 Hz, some nibbling at area of lead was observed at 50 Hz, and muscle capture was observed at 10 Hz. Thus, higher frequency modulation of the sympathetic chain appears to be tolerable to the animals in the study.

One of ordinary skill in the art will understand that, the modules and other circuitry shown and described herein can be implemented using software, hardware, and combinations of software and hardware. As such, the terms module and circuitry, for example, are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. A system may be configured to implement the method. The system may be configured with hardware, software, firmware, or any combination thereof to implement the method. In various embodiments, the methods are implemented using computer data in tangible media, that represents a sequence of instructions which, when executed by one or more processors cause the processor(s) to perform the respective method or at least a portion of the method. In various embodiments, the methods are implemented as a set (or sets) of instructions contained on a computer-accessible medium (or media) capable of directing a processor or other controller to perform the respective method or at least a portion of the method. In various embodiments, the medium or media include at least one of a magnetic medium, an electronic medium, or an optical medium.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method, comprising:
   inserting a trocar or cannulated needle through an entry point and advancing the trocar or cannulated needle toward a lateral part of lumber or thoracic spinal vertebra;
   inserting a lead through the trocar or cannulated needle, the lead including a distal electrode portion having at least one electrode and a strain relief proximate to the distal electrode portion;
   advancing the distal electrode portion of the lead toward a sympathetic chain in a lumbar region, orientating the distal electrode portion to orient electrodes toward the sympathetic chain under imaging guidance, and anchoring the lead in position to deliver electrical energy through the distal electrode portion to produce a modulation field at a portion of the sympathetic chain for modulating the sympathetic chain; and
   electrically connecting a proximal portion of the lead to an implantable modulation device.

2. The method of claim 1, wherein the entry point is supero-lateral to the iliac crest and to midline of spine.

3. The method of claim 1, wherein orientating includes orientating the distal electrode portion to orient electrodes away from a psoas muscle.

4. The method of claim 1, wherein anchoring includes anchoring the lead to a psoas tendon or a psoas muscle, or to a lateral portion of a vertebral body.

5. The method of claim 1, further comprising wrapping the distal electrode portion at least 180 degrees around the sympathetic chain.

6. The method of claim 5, wherein the distal electrode portion includes a shape memory to wrap around the sympathetic chain and further includes a channel to receive a wire to maintain the distal electrode portion in an unwrapped state, the method further including removing the wire to allow the distal electrode portion to wrap around the sympathetic chain.

7. The method of claim 1, wherein the distal electrode portion includes an extendible hook configured to extend from a lead body, the method further comprising extending the hook and placing the extended hook around at least a portion of the sympathetic chain, and retracting the hook toward the lead body.

8. The method of claim 1, wherein the distal electrode portion includes a hook and a movable clasp configured to move between and extended position and a retracted position, wherein the method further includes placing the hook to partially encircle the sympathetic chain when the movable clasp is in the retracted position, and extending the movable clasp.

9. The method of claim 1, further comprising delivering a chemical block, electrical block or cryotherapy block to the sympathetic chain in the lumbar region to test efficacy and determine if a patient is a candidate for sympathetic modulation therapy before inserting the trocar and inserting the lead through the trocar.

10. The method of claim 1, further comprising using a laparoscopic procedure, the laparoscopic procedure including introducing a laparoscope and light into the patient to visualize the distal electrode and the sympathetic chain.

11. The method of claim 1, further comprising using fluoroscopy, ultrasound or magnetic resonance imaging (MRI) to advance and implant the distal electrode portion of the lead to the sympathetic chain.

12. The method of claim 1, further comprising:
electrically modulating neural activity in the sympathetic chain using an implantable modulation device connected to the lead,
wherein electrically modulating includes delivering a neuromodulation energy at a frequency to reversibly block or reduce neural activity in the sympathetic chain.

13. The method of claim 12, wherein electrically modulating includes delivering the neuromodulation energy to provide a neurotransmitter depletion block.

14. The method of claim 13, wherein electrically modulating includes delivering the neuromodulation energy to provide a conduction block.

15. The method of claim 13, wherein electrically modulating includes initiating electrical modulation at a first frequency for a time period less than a minute, and then transitioning to a second frequency less than the first frequency.

16. The method of claim 13, further comprising receiving a patient command to initiate electrical modulation, and delivering the neuromodulation energy in response to the patient command or an automated system with feedback.

17. The method of claim 13, further comprising automatically stopping delivery of the neuromodulation energy after a programmed duration.

18. The method of claim 13, wherein the programmed duration includes a programmed period of time, a programmed number of delivered pulses, or a programmed amount of delivered charge.

19. The method of claim 13, further comprising:
sensing at least one physiological parameter to provide an indication of sympathetic nervous system activity or peripheral vascular tone or perfusion; and
automatically controlling the neuromodulation energy based on the indication of sympathetic nervous system activity or peripheral vascular tone or perfusion.

20. The method of claim 13, wherein delivering the neuromodulation energy to reversibly block or reduce neural activity in the sympathetic chain is part of a therapy to treat pain, hypertension, heart failure, peripheral vascular disease, ulcers or diabetes.

* * * * *